US008840907B2

(12) United States Patent
Pizza

(10) Patent No.: US 8,840,907 B2
(45) Date of Patent: Sep. 23, 2014

(54) ISOLATED PROTEIN AND COMPOSITIONS COMPRISING THE PROTEIN

(75) Inventor: Mariagrazia Pizza, Siena (IT)

(73) Assignee: Novartis Vaccines and Diagnostics S.r.l., Siena (IT)

( * ) Notice: Subject to any disclaimer, the term of this patent is extended or adjusted under 35 U.S.C. 154(b) by 0 days.

(21) Appl. No.: 13/366,252

(22) Filed: Feb. 3, 2012

(65) Prior Publication Data

US 2012/0195919 A1   Aug. 2, 2012

Related U.S. Application Data

(62) Division of application No. 10/488,786, filed as application No. PCT/IB02/03904 on Sep. 6, 2002.

(30) Foreign Application Priority Data

Sep. 6, 2001 (GB) .................................. 0121591.2

(51) Int. Cl.
*A61K 39/095* (2006.01)
*C07K 14/22* (2006.01)
*A61K 39/00* (2006.01)

(52) U.S. Cl.
CPC ................. *C07K 14/22* (2013.01); *A61K 39/00* (2013.01); *A61K 2039/53* (2013.01)
USPC .................................. 424/250.1; 424/197.11

(58) Field of Classification Search
None
See application file for complete search history.

(56) References Cited

U.S. PATENT DOCUMENTS

| | | | |
|---|---|---|---|
| 6,165,747 A | 12/2000 | Ingham et al. | |
| 6,248,329 B1 * | 6/2001 | Chandrashekar et al. . | 424/191.1 |
| 7,348,006 B2 | 3/2008 | Contorni et al. | |
| 7,576,176 B1 * | 8/2009 | Fraser et al. .................... | 530/350 |
| 7,785,608 B2 | 8/2010 | Zlotnick et al. | |
| 7,862,827 B2 * | 1/2011 | Giuliani et al. ............ | 424/250.1 |
| 8,226,960 B2 | 7/2012 | Masignani et al. | |
| 8,273,360 B2 | 9/2012 | Pizza et al. | |
| 8,398,988 B2 | 3/2013 | Contorni et al. | |
| 8,398,999 B2 | 3/2013 | Masignani et al. | |
| 8,563,007 B1 | 10/2013 | Zlotnick et al. | |
| 2004/0092711 A1 | 5/2004 | Arico et al. | |
| 2004/0110670 A1 | 6/2004 | Arico et al. | |
| 2004/0167068 A1 | 8/2004 | Zlotnick et al. | |
| 2005/0222385 A1 | 10/2005 | Pizza | |
| 2006/0051840 A1 | 3/2006 | Arico et al. | |
| 2006/0115475 A1 | 6/2006 | Carton et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0082014 A1 | 4/2007 | Costantino | |
| 2007/0253984 A1 | 11/2007 | Khandke et al. | |
| 2008/0241180 A1 | 10/2008 | Contorni | |
| 2009/0285845 A1 | 11/2009 | Masignani et al. | |
| 2010/0267931 A1 | 10/2010 | Arico et al. | |

FOREIGN PATENT DOCUMENTS

| | | |
|---|---|---|
| EP | 0196056 A | 10/1986 |
| EP | 0467714 | 1/1992 |
| EP | 0978565 A | 2/2000 |
| EP | 1645631 A2 | 4/2006 |
| EP | 1790660 | 5/2007 |
| EP | 2351767 A2 | 8/2011 |
| WO | WO-88/00238 A | 1/1988 |
| WO | WO-96/29412 A1 | 9/1996 |
| WO | WO-98/17805 | 4/1998 |
| WO | WO-99/57280 A | 11/1999 |
| WO | WO-00/22430 A2 | 4/2000 |
| WO | WO-00/66791 | 11/2000 |
| WO | WO-01/31019 | 5/2001 |
| WO | WO-01/52885 | 7/2001 |
| WO | WO-01/64920 A | 9/2001 |
| WO | WO-01/64922 A2 | 9/2001 |
| WO | WO-02/079242 A | 10/2002 |
| WO | WO-03/009869 A1 | 2/2003 |
| WO | WO-03/020756 A | 3/2003 |
| WO | WO-03/063766 | 8/2003 |
| WO | WO-2004/032958 A1 | 4/2004 |
| WO | WO-2004/048404 | 6/2004 |
| WO | WO-2006/024954 A2 | 3/2006 |
| WO | WO-2006/081259 A2 | 8/2006 |
| WO | WO-2007/060548 A2 | 5/2007 |
| WO | WO-2007/127665 A2 | 11/2007 |
| WO | WO-2008/149238 A2 | 12/2008 |
| WO | WO-2009/104097 A2 | 8/2009 |
| WO | WO-2010/028859 A1 | 3/2010 |
| WO | WO-2010/046715 A1 | 4/2010 |

OTHER PUBLICATIONS

Feng et al (Infection and Immunity, 64(1):363-365, 1996).*
Ellis, R.W. (Chapter 29 of "Vaccines" [Plotkin, S.A. et al. (eds) published by W. B. Saunders company (Philadelphia) in 1988).*
Nov. 17, 1997-NM_shotgun.dbs and Dec. 15, 1997-NM.dbs, located at <ftp://ftp.sanger.ac.uk/pub/pathogens/nm/old data/>.
Aasel et al. (1998). Abstract from the 11th International Pathogenic Neisseria Conference, Nice France, Nov. 1-6, 1998. pp. 37-38.
Ashton et al. (1983). "Immunogenic and protective properties of meningococcal serotype 2a protein in the hen-embryo model," J Med Microbiol 16(4):443-57.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.

(Continued)

*Primary Examiner* — Patricia A Duffy
(74) *Attorney, Agent, or Firm* — Morrison & Foerster LLP

(57) ABSTRACT

Two or more Neisserial proteins are joined such that they are translated as a single polypeptide chain. Hybrid proteins are represented by the formula $NH_2\text{-}A\text{-}[\text{-}X\text{-}L\text{-}]_n\text{-}B\text{-}COOH$ where X is an amino acid sequence, L is an optional linker amino acid sequence, A is an optional N-terminal amino acid sequence, B is an optional C-terminal amino acid sequence, and n is an integer greater than 1. Proteins where each of the n -X- moieties shares sequence identity to each other -X- moiety, the protein is a 'tandem protein'.

2 Claims, 7 Drawing Sheets

(56) References Cited

OTHER PUBLICATIONS

Beernink et al. (Jun. 2008). "Bactericidal antibody responses, induced by meningococcal recombinant chimeric factor H-binding protein vaccines," Infection and Immunity 76(6):2568-2575.

Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.

Beernick (Jul. 2010) "Impaired immungenicity of a meningococcal factor H-binding protein vaccine engineered to eliminate factor h binding," Clin Vac Immunol 17(7):1074-1078.

Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116 and 124.

Blythe et al. (2005). "Benchmarking B cell epitope prediction: underperformance of existing methods," Protein Sci. 14:246-248.

Boslego et al. (1991). "Gonorrhea Vaccines," Chapter 17 In *Vaccines and Immunotherapy*, Cryz S.J. (Ed.), Pergamon Press: New York, NY, pp. 211-223.

Cannon (1989). "Conserved Lipoproteins of Pathogenic Neisseria Species Bearing the H.8 Epitope: Lipid-Modified Azurin and H.8 Outer Membrane Protein," Clinical Microbiology Reviews 2 (Suppl.):S1-S4.

Cantini et al. (Mar. 2006). "Solution Structure of the Immunodominant Domain of Protective Antigen GNA 1870 of Neisseria meningitidis," *Journal of Biological Chemistry* 281(11): 7220-7227.

Cruse et al. (2003). Illustrated Dictionary of Immunology, $2^{nd}$ Ed. CRC Press, pp. 46, 166, and 382.

Database accession No. NMB1994 (cf. XP2231040) (Tettelin et al.), uploaded Oct. 1, 2000.

Declaration by Dr. Julian Parkhill dated Jun. 12, 2008, submitted in opposition proceedings for EP1645631, 2 pages.

Ellis (1988). Chapter 29 in Vaccines, Plotkin, S.A. et al. eds., W. B. Saunders Company: Philadelphia, PA. pp. 568-574.

Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.

Feavers et al. (2009). "Meningococcal protein antigens and vaccines," Vaccine 275:B42-B50.

Feng et al. (1996). "P55, an Immunogenic but Nonprotective 55-Kilodalton *Borrelia burgdorferi* Protein in Murine Lyme Disease," Infection and Immunity. 64(1):363-365.

Fleischmann et al. (1995). "Whole-Genome Random Sequencing and Assembly of *Haemophilus influenzae* Rd," Science 269:496-501.

Fletcher et al. (2004). "Vaccine Potential of the Neisseria meningitidis 2086 Lipoprotein," *Infection and Immunity* 72(4): 2088-2100.

Fontana et al. (2002). A genomic approach Abstract from the $13^{th}$ International Pathogenic Neisseria Conference, Oslo, Norway, Sep. 1-6, 2002. p. 248.

Giuliani et al. (2006). "A universal vaccine for serogroup B meningococcus," PNAS 103(29):10834-10839.

Giuliani et al. (Feb. 2005). "The Region Comprising Amino Acids 100 to 255 of Neisseria meningitidis Lipoprotein GNA 1870 Elicits Bactericidal Antibodies," *Infection and Immunity* 73(2): 1151-1160.

Greenbaum et al. (2007). "Towards a consensus on datasets and evaluation metrics for developing B-cell epitope prediction tools" J Mol Recognition 20(2):75-82.

Greenspan et al. (1999). "Defining Epitopes: It's Not as Easy as It Seems," Nature Biotechnology 17:936-937.

Guillen et al. (1996). "Expression in *Escherichia coli* and Immunological Characterization of a Hybrid Class I-P64K Protein from Neisseria Meningitidis," *Biotecnologia Aplicada*13(4):271-275.

Hou et al. (2005) "Protective antibody responses elicited by a meningococcal outer membrane vesicle vaccine with overexpressed genome-derived neisserial antigen 1870," J Infect Dis 192(4):580-90.

Jacobsson et al. (2009). "Prevalence and sequence variations of the genes encoding the five antigens included in the novel 5CVMB vaccine covering group B meningococcal disease" Vaccine. 27:1579-1584.

JCVI-CMR website showing Z2491 Sanger sequence (http://cmr.jcvi.org/tigr-scripts/CMR/shared/Genomes.cgi and links). (2010).

Jiang et al., (2010) "Broad vaccine coverage predicted for a bivalent recombinant factor H binding protein based vaccine to prevent serogroup B meningococcal disease" Vaccine 28:6086-6093.

Koeberling et al. (2007). "Improved immunogenicity of a H44/76 group B outer membrane vesicle vaccine with over-expressed genome-derived Neisserial antigen 1870," Vaccine 25(10):1912-1920.

Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.

Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.

Masignani V. (Mar. 17, 2003). "Vaccination against Neisseria meningitidis using three variants of the lipoprotein GNA1870," J. Exp. Med. 197(6):789-799.

Morley, S. et al. (Dec. 12, 2001). "Vaccine prevention of meningococcal disease, coming soon?" *Vaccine* 20(5-6):666-687.

Murphy et al., (2009) "Sequence diversity of the factor H binding protein vaccine candidate in epidemiologically relevant strains of serogroup B Neisseria meningitidis" J Infect Dis 200:379-389.

Nassif (2000). "A Furtive Pathogen Revealed," Science 287: 1767-1768.

Notice of Opposition against European Patent EP 1645631, granted on Oct. 24, 2007. Opposition filed on Jul. 23, 2008. 20 pages.

Novartis (Oct. 9, 2008) "New Phase II data show Novartis investigational Meningitis B vaccine may also protect infants six months and older," Media Release, 4 pages.

Pajon et al., "Frequency of factor H-binding protein modular groups and susceptibility to cross-reactive bactericidal activity in invasive meningococcal isolates" Vaccine 28 (2010):2122-2129.

Pannekoek (1995). "Construction of recombinant neisserial Hsp60 proteins and mapping of antigenic domains," Mol Microbiol 5(2):277-85. Abstract.

Parkhill, J. et al. (Mar. 2000). "Complete DNA Sequence of a Serogroup A Strain of Neisseria meningitides Z2491," *Nature* 404(6777):502-506.

Parkhill, "Campylobacter jejuni genome sequence at the Sanger Centre," Post on BIOSCI/Bionet of May 8, 1998.

Patentees' Response to Opposition against European Patent EP 1645631, granted on Oct. 24, 2007. 13 pages.

Pettersson et al. (1993). "Molecular Characterization of the 98-Kilodalton Iron-Regulated Outer Membrane Protein of Neisseria meningitidis," Infection and Immunity 61(11):4724-4733.

Pizza et al. (2000). "Identification of Vaccine Candidates Against Serogroup B Meningococcus by Whole-Genome Sequencing," Science 287(5459):1816-1820.

Pizza et al. (2008) "Factor H-binding protein, a unique meningococcal vaccine antigen" Vaccine 26S:I46-8.

Progress through the Sanger Institute FTP server (May 12, 2009), 15 pages.

PSORT analysis of 200 of the sequences disclosed in PCT/US99/09346 (Jan. 1, 2010), 209 psges.

PSORT analysis of SEQ ID Nos. 4 and 6, and of 'Contig295' 300mer (May 8, 2009), 5 pages.

PSORT prediction result for SEQ ID No. 2 (Mar. 30, 2010), 1 page.

Response to Communication, filed in EP Application No. 07075161. 5. Oct. 28th, 2009.

Rinaudo et al. (2009). "Vaccinology in the genome era", The Journal of Clinical Investigation, 119(9):2515-2525.

Romero et al., "Current status of Meningococcal group B vaccine candidates: capsular or noncapsular?" *Clin. Microbiol. Rev.* 7(4):559-575, 1994.

(56) References Cited

OTHER PUBLICATIONS

Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.
Sequence for "Putative Lipoprotein [*Neisseria Meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
*Sigma Catalog* (1996). pp. 1957-1963.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Telford et al. (2003). "Genomic and Proteomics in Vaccine Design" in *New Bacterial Vaccines*, edited by Ellis et al. Kleweur Academic/Plenum Publishers, USA. pp. 1-11.
Tettelin et al. (Mar. 10, 2000). "Complete Genome Sequence of Neisseria meningitidis Serogroup B Strain MC58," Science 287(5459):1809-1815.
The printed output from the NCBI open reading frame finder (Oct. 20, 2008), 12 pages.
United States Office Action mailed on Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998.
Welsch et al. (2004). "Protective Activity of Monclonal Antibodies to Genome-Derived Neisserial Antigen 1870, a Neisseria meningitidis Candidate Vaccine," *The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Zhu et al. (2005) "Evaluation of recombinant lipidated P2086 protein as a vaccine candidate for group B Neisseria meningitidis in a murine nasal challenge model," Infect Immun 73(10):6838-45.
Zollinger (1997). "New and Improved Vaccines Against Meningococcal Disease" in *New Generation Vaccines*, 2nd Ed., edited by Levine et al., Marcel Dekker, New York. pp. 469-488.
Bjune G, et al. (1991). Effect of outer membrane vesicle vaccine against group B meningococcal disease in Norway. Lancet 338: 1093-1096.
Borrow and Carlone. (2001). Serogroup B and C bactericidal assays, p. 289-304. In A. Pollard and M. Maiden (ed.), Meningococcal vaccines. Humana Press, Totowa, NJ.
Borrow R, Balmer P, Miller E. Meningococcal Surrogates of Protection—Serum Bactericidal Activity. Vaccine 2005;23:2222-2227.
Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.
De Moraes JC, et al. (1992). Protective efficacy of a serogroup B meningococcal vaccine in Sao Paulo, Brazil. Lancet 340: 1074-1078.
European Medicines Agency, (Nov. 16, 2012). "European Medicines Agency recommends approval of first vaccine for meningitis B," Press Release, 2 pages.

Frasch, CE, Borrow, R, Donnelly J (2009). Bactericidal antibody is the immunologic surrogate of protection against meningococcal disease. Vaccine 27(Supplement 2): B112-B116.
Goldschneider I, Gotschlich EC, Artenstein MS. (1969). Human immunity to the meningococcus. I. The role of humoral immunity. J Exp Med 129:1307-1326.
Goldschneider I, Gotschlich EC, Artenstein MS. (1969). Human immunity to the meningococcus. II. Development of natural immunity. J Exp Med 129:1327-1348.
Granoff, DM. (2009). Relative importance of complement-mediated bactericidal and opsonic activity for protection against meningococcal disease. Vaccine 27(Supplement 2): B117-B125.
Holst et al. (2003). "Serum bactericidal activity correlates with the vaccine efficacy of outer membrane vesicle vaccines against Neisseria meningitidis serogroup B disease," Vaccine 21(7-8):734-737.
Milagres, L. G., et al. (1994). Immune response of Brazilian children to a Neisseria meningitidis serogroup B outer membrane protein vaccine: comparison with efficacy. Infect. Immun. 62(10):4419-4424.
O'Hallahan J, et al. (2004). The strategy to control New Zealand's epidemic of Group B meningococcal disease. PIDJ 23: S293-S298.
Oster P, et al. (2007). Immunogenicity and safety of a strain-specific MenB OMV vaccine delivered to under 5-year olds in New Zealand. Vaccine. 25:3075-9.
Sierra GV, et al. (1991). Vaccine against group B Neisseria meningitidis: protection trial and mass vaccination results in Cuba. NIPH Ann 14: 195-207.
World Health Organization official document. 1999. Standarization and validation of serological assays for the evaluation of immune responses to Neisseria meningitidis serogroup A/C vaccines. Mar. 8-9, 1999.
Aderson et al. (2010). "Effectiveness of a bivalent factor H binding protein vaccine across Neisseria meningitidis serogroups," 17th International Pathogenic Neisseria Conference 2010, p. 196.
Ala'Aldeen et al. (2010) "Human antibody response to the meningococcal factor H binding protein (LP2086) during invasive disease, colonization and carriage," Vaccine 28:7667-75.
Ambrose et al. (2006). "Characterization of LP2086 expression in Neisseria meningitidis," 15th International Pathogenic Neisseria Conference 2006, p. 103.
Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.
Anderson et al. (2009). "Epidemiology of the serogroup B Neisseria meningitidis (MnB) factor H binding protein and implications for vaccine development," European Society for Paediatric Infectious Disease Symposium 2009, p. 505.
Anderson et al. (2009). "Development of a factor H binding protein vaccine for borad protection against invasive Neisseria meningitidis serogroup B (MnB) disease," 10th European Meningococcal Disease Society Congress 2009, p. 39.
Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.
Anderson et al. (2013) "Potential impact of the bivalent rLP2086 vaccine on Neisseria meningitidis carriage and invasive serogroup B disease," Hum Vacc Immunotherap 9:471-9.
Appendix I to Statement of Grounds of Appeal filed by df-mp on Sep. 28, 2012, in relation to EP1645631, 1 pages.
Appendix II to Statement of Grounds of Appeal filed by df-mp on Sep. 28, 2012, in relation to EP1645631, 2 pages.
Bentley et al. (2004). Identification of two immunologically distinct domains on the LP2086 outer membrane lipoprotein of Neisseria meningitidis, 14th International Pathogenic Neisseria Conference 2004, p. 144.
Bouvier et al. (1991). "A gene for a new lipoprotein in the dapA-purC interval of the *Escherichia coli* chromosome," J Bacteriol 173(17):5523-5531.

(56) References Cited

OTHER PUBLICATIONS

Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1>.
Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.
Cordis, "Preparation of meningococcal antigens," posted online on Feb. 2, 2005, 2 pages.
Declaration by Dr. Ellen Murphy, Ph.D., dated Sep. 14, 2011, submitted in opposition proceedings for EP1645631, 4 pages.
Declaration by E. Richard Moxon dated Feb. 16, 2013, submitted in opposition proceedings for EP1645631, 5 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from Neisseria meningitidis serogroup B as a novel vaccine candidate," Vaccine 25:8420-8431.
Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Bicrobiol 148:119-131.
Dlawer et al. (2010). "Human antibody responses to the meningococcal factor H binding protein LP2086 during invasive disease," 17th International Pathogenic Neisseria Conference 2010, p. 130.
Facts and Submissions dated May 21, 2012, in relation to EP1645631, 30 pages.
Fraser et al. (1997). "Genomic sequence of a lyme disease spirochaete, *Borrelia burgdorferi*," Nature 390:580-586.
Fraser et al. (1998). "Complete genome sequence of *Treponema pallidum*, the syphilis spirochete," Science 281:375-388.
GenPept accession No. AAF42204, "hypothetical protein NMB1870 [Neisseria meningitidis MC58]," retrieved on Sep. 26, 2012, 2 pages.
Giuliani et al. (2010). "Measuring antigen-specific bactericidal responses to a multicomponent vaccine against serogroup B meningococcus," Vaccine 28:5023-5030.
Gold and Stormo (1987). "Translation Initiation", in *Escherichia con* and *Salmonella typhimurium*, Cellular and Molecular Biology, Ed. Neidhardt, pp. 1302-1307.
Gorringe et al. (2009). "16th International Pathogenic Neisseria Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Harris et al. (2008). "Development and qualification of serum bactericidal assays for Neisseria meningitidis serogroup B," 16th International Pathogenic Neisseria Conference 2008, p. 268-269.
Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Hung et al. (2011). "The Neisseria meningitidis macrophage infectivity potentiator protein induces cross-strain serum bactericidal sctivity and is a potential serogroup B vaccine candidate," Infect Immun 79(9):3784-3791.
Jansen et al. (2008). "Bivalent recombinant LP2086 vaccine to provide broad protection against Neiseria meningitidis B disease: immunological correlates of protection and how to assess coverage against invasive MnB strains," 16th International Pathogenic Neisseria Conference 2008, p. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, p. 57-58.
Johnson et al. (1999). "Analysis of the human Ig isotype response to lactoferrin binding protein A from Neisseria meningitidis," FEMS Immun. Med. Microbial. 25(4): 349-354.
Jones et al. (2005). "Effects of adsorption to aluminum salt adjuvants on the structure and stability of model protein antigens," J Biol Chem 280(14):13406-13414.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Klein et al. (2000). "Analysis of aluminum hydroxyphosphate vaccine adjuvants by 27Al MAS NMR," J Pharma Sci 89(3):311-321.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Liebl et al. (1997). "Properties and gene structure of the Thermotoga maritima alpha-amylase AmyA, a putative lipoprotein of a hyperthermophilic bacterium," J Bacteriol 179(3):941-948.
Marshall et al. (2008). "A randomized, placebo-controlled, double-blind, phase 1 trial of ascending doses of meningococcal group B

(56) References Cited

OTHER PUBLICATIONS rLP2086 vaccine in healthy adults," 16th International Pathogenic Neisseria Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic Neisseria Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Milagres et al. (1998). "Specificity of bactericidal antibody response to serogroup B meningococcal strains in Brazilian children after immunization with an outer membrane vaccine," Infection and Immun. 66(10): 4755-4781.
Munkley, et al. (1991). "Blocking of bactericidal killing of Neisseria meningitidis by antibodies directed against slacc 4 outer membrane proteins," Microbial Pathogenesis 11: 447-452.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in N. meningitidis Carriage Isolates," 17th International Pathogenic Neisseria Conference 2010, p. 96.
Novartis (Jan. 22, 2013) "Novartis receives EU approval for Bexsero®, first vaccine to prevent the leading cause of life-threatening meningitis across Europe," Media Release, 3 pages.
Pajon et al. (2012). "Design of meningococcal factor H binding protein mutant vaccines that do not bind human complement factor H," Infect Immun 80:2667-2677.
Pettersson, et al. (2006). "Vaccine potential of the Neisseria meningitidis lactoferrin-binding proteins LbpA and LbpB," Vaccine 24(17):3545-3557.
Pillai et al. (2005) "Outer membrane protein (OMP) based vaccine for Neisseria meningitidis serogroup B," Vaccine 23(17-18):2206-2209.
Prosite, "ScanProsite Results Viewer: USERSEQ1 (280aa)," retrieved on Jun. 21, 2012, 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.

Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the mengococcus in vitro and in ex vivo and in vivo models of infection," Vaccine 28(12):2416-2427.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of *Erwinia chrysanthemi* 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Tan et al. (2010). "Advances in the development of vaccines against Neisseria meningitidis," NEJM 362(16):1511-1520.
TIGR website as of 1998, 8 pages.
Vermont et al. (2003). "Cross-reactivity of antibodies against PorA after vaccination with a meningococcal B outer membrane vesicle vaccine," Infect Immun 71(4):1650-1655.
Von Heijne (1989). "The structure of signal peptides from bacterial lipoproteins," Protein Engineering 2(7):531-534.
Wang et al. (2010). "Prevalence and genetic diversity of candidate vaccine antigens among invasive Neisseria meningitidis isolates in the United States," 17th International Pathogenic Neisseria Conference 2010, p. 122.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.

(56) References Cited

OTHER PUBLICATIONS

Zhu et al. (2006) "Intranasal immunization of mice with recombinant lipidated P2086 protein reduces nasal colonization of group B Neisseria meningitidis," Vaccine 24:5420-5.

Zhu et al. (2006). "Effective immunization strategy against group B Neisseria meningitidis using purified recombinant lipidated P2086 protein," 15th International Pathogenic Neisseria Conference 2006, p. 47.

Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.

Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.

* cited by examiner

FIGURE 1

```
                  . . . .10. . . .20. . . .30. . . .40. . . .50
312294     1:MTRSKPVNRTAFCCLSLTAALILTACSSGGGGVAADIGAGLADALTAPL : 50
96          :~~~~~~~~~~~~~~~~~~~~~~~~~~~~~~~~~~~~~~~~~~~~~~~~~:
96217      1:MTRSKPVNRTAFCCLSLTAALILTACSSGGGGVAADIGAGLADALTAPL : 50
M1090      1:MTRSKPVNRTAFCCLSLTAALILTACSSGGGGVAADIGAGLADALTAPL : 50
95N477     1:MTRSKPVNRTAFCCLSLTAALILTACSSGGGGVAADIGAGLADALTAPL : 50
C11        1:MTRSKPVNRTAFCCLSLTAALILTACSSGGGGVAADIGAGLADALTAPL : 50
599        1:MTRSKPVNRTAFCCLSLTAALILTACSSGGGGVAADIGAGLADALTAPL : 50
24         1:~~~~~~~~~~~~~~~~~~~~~~~~~~~~~~~~~~~~~~~ADALTAPL : 11
1000       1:MTRSKPVNRTAFCCLSLTAALILTACSSGGGGVAADIGAGLADALTTPL : 50
M1096      1:MTRSKPVNRTAFCCLSLTAALILTACSSGGGGVAADIGAGLADALTTPL : 50
BZ232      1:MTRSKPVNRTAFCCLSLTAALILTACSSGGGGVAADIGAGLADALTAPL : 50
NGH38      1:MTRSKPVNRTAFCCLSLTAALILTACSSGGGGVAADIGAGLADALTAPL : 50
25         1:~~~~~~~~~~~~~~~~~~~~~~~~~~~~~~~~VAADIGAGLADALTAPL : 18
6700       1:MTRSKPVNRTAFCFSLTAALILTACSSGGGGVAADIGAGLADALTAPL : 50
93114      1:MTRSKPVNRTAFCFSLTAALILTACSSGGGGVAADIGAGLADALTAPL : 50
21         1:~~~~~VNRTAFCCLSLTALILTACSSGGGGVAADIGAGLADALTAPL : 44
3999        :~~~~~~~~~~~~~~~~~~~~~~~~~~~~~~~~~~~~~~~~~~~~~~~~~:
3000        :~~~~~~~~~~~~~~~~~~~~~~~~~~~~~~~~~~~~~~~~~~~~~~~~~:
7           :~~~~~~~~~~~~~~~~~~~~~~~~~~~~~~~~~~~~~~~~~~~~~~~~~:
7200        :~~~~~~~~~~~~~~~~~~~~~~~~~~~~~~~~~~~~~~~~~~~~~~~~~:
M198172    1:MTRSKPVNRTAFCCLSLTAALILTACSSGGGGVAADIGAGLADALTAPL : 50
BZ133      1:MTRSKPVNRTAFCCLSLTAALILTACSSGGGGVAADIGAGLADALTAPL : 50
220173I    1:MTRSKPVNRTAFCCLSLTALILTACSSGGGGVAADIGAGLADALTAPL : 50

. . . .60. . . .70. . . .80. . . .90. . . 100
312294    51:IKDKSLQSLTLDQSVRKNEKLKLAAQGAEKTYGNGDSLNTGKLKNDKVSR:100
96         1:~KDKSLQSLTLDQSVRKNEKLKLAAQGAEKTYGNGDSLNTGKLKNDKVSR: 49
96217     51:IKDKSLQSLTLDQSVRKNEKLKLAAQGAEKTYGNGDSLNTGKLKNDKVSR:100
M1090     51:IKDKSLQSLTLDQSVRKNEKLKLAAQGAEKTYGNGDSLNTGKLKNDKVSR:100
95N477    51:IKDKSLQSLTLDQSVRKNEKLKLAAQGAEKTYGNGDSLNTGKLKNDKVSR:100
C11       51:IKDKSLQSLTLDQSVRKNEKLKLAAQGAEKTYGNGDSLNTGKLKNDKVSR:100
599       51:IKDKGLQSLTLDQSVRKNEKLKLAAQGAEKTYGNGDSLNTGKLKNDKVSR:100
24        12:IKDKSLQSLTLDQSVRKNEKLKLAAQGAERTYGNGDSLNTGKLKNDKVSR: 61
1000      51:IKDKSLQSLTLDQSVRKNEKLKLAAQGAEKTYGNGDSLNTGKLKNDKVSR:100
M1096     51:IKDKSLQSLTLDQSVRKNEKLKLAAQGAEKTYGNGDSLNTGKLKNDKVSR:100
BZ232     51:IKDKSLQSLTLDQSVRKNEKLKLAAQGAEKTYGNGDSLNTGKLKNDKVSR:100
NGH38     51:IKDKSLQSLTLDQSVRKNEKLKLAAQGAEKTYGNGDSLNTGKLKNDKVSR:100
25        19:IKDKGLQSLMLDQSVRKNEKLKLAAQGAEKTYGNGDSLNTGKLKNDKVSR: 68
6700      51:IKDKSLQSLTLDQSVRKNEKLKLAAQGAEKTYGNGDSLNTGKLKNDKVSR:100
93114     51:IKDKSLQSLTLDQSVRKNEKLKLAAQGAEKTYGNGDSLNTGKLKNDKVSR:100
21        45:IKDKGLQSLTLDQSVRKNEKLKLAAQGAEKTYGNGDSLNTGKLKNDKVSR: 94
3999       1:~~KGLQSLTLDQSVRKNEKLKLAAQGAEKTYGNGDSLNTGKLKNDKVSR: 48
3000       1:~KKGLQSLTLDQSVRKNEKLKLAAQGAEKTYGNGDSLNTGKLKNDKVSR: 49
7          1:~~~~~LQSLTLDQSVRKNEKLKLAAQGAEKTYGNGDSLNTGKLKNDKVSR: 45
7200       1:~~~~~LQSLTLDQSVRKNEKLKLAAQGAEKTYGNGDSLNTGKLKNDKVSR: 45
M198172   51:IKDKSLQSLTLDQSVRKNEKLKLAAQGAEKTYGNGDSLNTGKLKNDKVSR:100
BZ133     51:IKDKSLQSLTLDQSVRKNEKLKLAAQGAEKTYGNGDSLNTGKLKNDKVSR:100
220173I   51:IKDKGLQSLTLDQSVRKNEKLKLAAQGAEKTYGNGDSLNTGKLKNDKVSR:100
```

FIGURE 1 CONTD...

```
              ....110...120...130...140.....150
312294   101:FDFIRQIEVDGQLITLESGEFQIYKQDHSAVVALQIEK NN DKIDSLIN:150
96        50:FDFIRQIEVDGQLITLESGEFQIYKQDHSAVVALQIEK NN DKIDSLIN: 99
96217    101:FDFIRQIEVDGQLITLESGEFQIYKQDHSAVVALQIEK NN DKIDSLIN:150
M1090    101:FDFIRQIEVDGQLITLESGEFQIYKQDHSAVVALQIEK NN DKIDSLIN:150
95N477   101:FDFIRQIEVDGQLITLESGEFQIYKQDHSAVVALQIEK NN DKIDSLIN:150
C11      101:FDFIRQIEVDGQLITLESGEFQIYKQDHSAVVALQIEK NN DKIDSLIN:150
599      101:FDFIRQIEVDGQLITLESGEFQIYKQDHSAVVALQIEK NN DKIDSLIN:150
24        62:FDFIRQIEVDGQLITLESGEFQIYKQDHSAVVALQIEK NN DKIDSLIN:111
1000     101:FDFIRQIEVDGQTITLASGEFQIYKQNHSAVVALQIEK NN DKIDSLIN:150
M1096    101:FDFIRQIEVDGQTITLASGEFQIYKQNHSAVVALQIEK NN DKIDSLIN:150
BZ232    101:FDFIRQIEVDGQTITLASGEFQIYKQNHSAVVALQIEK NN DKIDSLIN:150
NGH38    101:FDFIRQIEVDGQTITLASGEFQIYKQNHSAVVALQIEK NN DKIDSLIN:150
25        69:FDFIRQIEVDGQTITLASGEFQIYKQNHSAVVALQIEK NN DKIDSLIN:118
6700     101:FDFIRQIEVDGQLITLESGEFQVYKQSHSALTALQTEQEQD EHSGKMVA:150
93114    101:FDFIRQIEVDGQLITLESGEFQVYKQSHSALTALQTEQEQD EHSGKMVA:150
21        95:FDFIRQIEVDGQLITLESGEFQVYKQSHSALTAFQTEQ QDSEHSGKMVA:144
3999      49:FDFIRQIEVDGQLITLESGEFQVYKQSHSALTAFQTEQ QDSEHSGKMVA: 98
3000      50:FDFIRQIEVDGQLITLESGEFQVYKQSHSALTAFQTEQ QDSEHSGKMVA: 99
7         46:FDFIRQIEVDGQLITLESGEFQVYKQSHSALTAFQTEQ QDSEHSGKMVA: 95
7200      46:FDFIRQIEVDGQLITLESGEFQVYKQSHSALTAFQTEQ QDSEHSGKMVA: 95
M198172  101:FDFIRQIEVDGQLITLESGEFQVYKQSHSALTALQTEQVQDSEHSGKMVA:150
BZ133    101:FDFIRQIEVDGQLITLESGEFQVYKQSHSALTALQTEQVQDSEHSGKMVA:150
220173I  101:FDFIRQIEVDGQLITLESGEFQVYKQSHSALTAFQTEQ QDSEHSGKMVA:150

...160....170...180....190...200
312294   151:QRSFLVSGLGGEHTAFNQLP G.KAEYHGKAFSSDD AGGKLTYTIDFAAK:199
96       100:QRSFLVSGLGGEHTAFNQLP G.KAEYHGKAFSSDD AGGKLTYTIDFAAK:148
96217    151:QRSFLVSGLGGEHTAFNQLP G.KAEYHGKAFSSDD AGGKLTYTIDFAAK:199
M1090    151:QRSFLVSGLGGEHTAFNQLPS .KAEYHGKAFSSDD GGKLTYTIDFAAK:199
95N477   151:QRSFLVSGLGGEHTAFNQLPS .KAEYHGKAFSSDDPNGRLHYSIDFTKK:199
C11      151:QRSFLVSGLGGEHTAFNQLPS .KAEYHGKAFSSDDPNGRLHYSIDFTKK:199
599      151:QRSFLVSGLGGEHTAFNQLPS .KAEYHGKAFSSDDPNGRLHYSIDFTKK:199
24       112:QRSFLVSGLGGEHTAFNQLPS .KAEYHGKAFSSDDPNGRLHYSIDFTKK:160
1000     151:QRSFLVSGLGGEHTAFNQLP .KAEYHGKAFSSDDPNGRLHYSIDFTKK:199
M1096    151:QRSFLVSGLGGEHTAFNQLP .KAEYHGKAFSSDDPNGRLHYSIDFTKK:199
BZ232    151:QRSFLVSGLGGEHTAFNQLP .KAEYHGKAFSSDDPNGRLHYSIDFTKK:199
NGH38    151:QRSFLVSGLGGEHTAFNQLP .KAEYHGKAFSSDDPNGRLHYSIDFTKK:199
25       119:QRSFLVSGLGGEHTAFNQLP .KAEYHGKAFSSDDPNGRLHYSIDFTKK:167
6700     151:KRRFKIGDIAGEHTSFDKLP KDVMATYRGTAFGSDD AGGKLTYTIDFAAK:200
93114    151:KRRFKIGDIAGEHTSFDKLP KDVMATYRGTAFGSDD AGGKLTYTIDFAAK:200
21       145:KRQFRIGDIAGEHTSFDKLP GRATYRGTAFGSDD GGKLTYTIDFAAK:194
3999      99:KRQFRIGDIAGEHTSFDKLP GRATYRGTAFGSDD GGKLTYTIDFAAK:148
3000     100:KRQFRIGDIAGEHTSFDKLP GRATYRGTAFGSDD GGKLTYTIDFAAK:149
7         96:KRQFRIGDIAGEHTSFDKLP GRATYRGTAFGSDD GGKLTYTIDFAAK:145
7200      96:KRQFRIGDIAGEHTSFDKLP GRATYRGTAFGSDD GGKLTYTIDFAAK:145
M198172  151:KRQFRIGDIAGEHTSFDKLP GRATYRGTAFGSDD SGKLTYIIDFAAK:200
BZ133    151:KRQFRIGDIAGEHTSFDKLP GRATYRGTAFGSDD SGKLTYIIDFAAK:200
220173I  151:KRQFRIGDIAGEHTSFDKLP GRATYRGTAFGSDD GGKLTYIIDFAAK:200
```

FIGURE 1 CONTD...

```
                . . . 210 . . . 220 . . . 230 . . . 240 . . . 250
312294   200:QGHGKIEHLKTPEQNVELAAAELKADEKSHAVILGDTRYGSEEKGTYHLA:249
96       149:QGHGKIEHLKTPEQNVELAAAELKADEKSHAVILGDTRYGSEEKGTYHLA:198
96217    200:QGHGKIEHLKTPEQNVELAAAELKADEKSHAVILGDTRYGSEEKGTYHLA:249
M1090    200:QGHGKIEHLKTPEQNVELASAELKADEKSHAVILGDTRYGGEEKGTYHLA:249
95N477   200:QGYGRIEHLKTPEQNVELASAELKADEKSHAVILGDTRYGGEEKGTYHLA:249
C11      200:QGYGRIEHLKTPEQNVELASAELKADEKSHAVILGDTRYGGEEKGTYHLA:249
599      200:QGYGRIEHLKTPEQNVELASAELKADEKSHAVILGDTRYGGEEKGTYHLA:249
24       161:QGYGRIEHLKTPEQNVELASAELKADEKSHAVILGDTRYGGEEKGTYHLA:210
1000     200:QGYGRIEHLKTPEQNVELASAELKADEKSHAVILGDTRYGGEEKGTYHLA:249
M1096    200:QGYGRIEHLKTPEQNVELASAELKADEKSHAVILGDTRYGGEEKGTYHLA:249
BZ232    200:QGYGRIEHLKTPEQNVELASAELKADEKSHAVILGDTRYGGEEKGTYHLA:249
NGH38    200:QGYGRIEHLKTPEQNVELASAELKADEKSHAVILGDTRYGGEEKGTYHLA:249
25       168:QGYGRIEHLKTPEQNVELASAELKADEKSHAVILGDTRYGGEEKGTYHLA:217
6700     201:QGHGKIEHLKSPELNVELATAYIKPDEKHHAVISGSVLYNQDEKGSYSLG:250
93114    201:QGHGKIEHLKSPELNVELATAYIKPDEKHHAVISGSVLYNQDEKGSYSLG:250
21       195:QGNGKIEHLKSPELNVDLAAADIKPDGKRHAVISGSVLYNQAEKGSYSLG:244
3999     149:QGNGKIEHLKSPELNVDLAAADIKPDGKRHAVISGSVLYNQAEKGSYSLG:198
3000     150:QGNGKIEHLKSPELNVDLAADIKPDGKRHAVISGSVLYNQAEKGSYSLG:199
7        146:QGNGKIEHLKSPELNVDLAADIKPDGKRHAVISGSVLYNQAEKGSYSLG:195
7200     146:QGNGKIEHLKSPELNVDLAADIKPDGKRHAVISGSVLYNQAEKGSYSLG:195
M198172  201:QGHGKIEHLKSPELNVDLAASDIKPDKKRHAVISGSVLYNQAEKGSYSLG:250
BZ133    201:QGHGKIEHLKSPELNVDLAASDIKPDKKRHAVISGSVLYNQAEKGSYSLG:250
220173I  201:QGNGKIEHLKSPELNVDLAADIKPDGKRHAVISGSVLYNQAEKGSYSLG:250

. . . 260 . . . 270 . . . 280
312294   250:LFGDRAQEIAGSATKIGEKVIECIIG  :279
96       199:LFGDRAQEIAGSAT~~~~~~~~~~~~~~~:212
96217    250:LFGDRAQEIAGSATKIGEKVIECIIG  :279
M1090    250:LFGDRAQEIAGSATVIREKVIECIIGK :279
95N477   250:LFGDRAQEIAGSATVIREKVIECIIGK :279
C11      250:LFGDRAQEIAGSATVIREKVIECIIGK :279
599      250:LFGDRAQEIAGSATVIREKVIECIIAG :279
24       211:LFGDRAQEIAGSATVIREKVIET~~~~~~:234
1000     250:LFGDRAQEIAGSATVIREKVIECIIG  :279
M1096    250:LFGDRAQEIAGSATVIREKVIECIIGK :279
BZ232    250:LFGDRAQEIAGSATVIREKVIECIIGK :279
NGH38    250:LFGDRAQEIAGSATVIREKVIECIIGK :279
25       218:LFGDRAQEIAGSATVIREKVIECIIG  :247
6700     251:IFGGQAQEVAGGAEETANGIRHILLAK :280
93114    251:IFGGQAQEVAGGAEETANGIRHILLAK :280
21       245:IFGGKAQEVAGGAETVNGIRHILLAK  :274
3999     199:IFGGKAQEVAGGAETVNGIRHILLAK  :228
3000     200:IFGGKAQEVAGGAETVNGIRHILLAK  :229
7        196:IFGGKAQEVAGGAETVNGIRHILLAK  :225
7200     196:IFGGKAQEVAGGAETVNGIRHILLAK  :225
M198172  251:IFGGQAQEVAGGAEETANGIRHILLAK :280
BZ133    251:IFGGQAQEVAGGAEETANGIRHILLAK :280
220173I  251:IFGGKA~~~~~~~~~~~~~~~~~~~~~~:256
```

FIGURE 2

```
         10        20        30        40        50        60        70
         |         |         |         |         |         |         |
TCCGCCGCATTACCTTATAAAATAAAACATCCCTCTCAAGCAGTCTGATAATGTTTGGATTGCTTGAGATTGATGAG
•••••••••••••••••••••••••••••••••••••••••••••••••••••••••••••••••••••••••••
TCCGCCGCATTACCTTATAAAATAAAACATCCCTCTCAAGCAGTCTGATAATGTTTGGATTGCTTGAGATTGATGAG 80        90       100       110       120       130       140       150
      |         |         |         |         |         |         |         |
TGATGGTGTTAAATTCAAACTTTAAATTAATAACTTATGGGAAATTTCTTATTTATATAGAGGCATTAGTTGCCAAC
• •••••••••••••• •••••••••••••••••••••••••••••••••••• ••••••••••••••••••••••
TAATGGTGTTAAATTCAACCTTTAAATTAATAACTTATGGGAAATTTCTTA----TATAGAGGCATTAGTTGCCAAC 160       170       180       190       200       210       220       230
         |         |         |         |         |         |         |         |
AAGATGAGCAAAATAATGGACAGTTAAAACCTAAAGGTAATAAAGCTGAAGTTGCAATTCGTTATGATGGTAAGTTT
•••••••••••••••••••••••••••••••••••••••••••••••••••••••••••••••••••••••••••
AAGATGAGCAAAATAATGGACAGTTAAAACCTAAAGGTAATAAAGCTGAAGTTGCAATTCGTTATGATGGTAAGTTT 240       250       260       270       280       290       300
        |         |         |         |         |         |         |
AAATATGATGGTAAAGCTACACATGGTCCAAGTGTGAAGAATGCAGTTTACGCCCATCAAATTGAAACAGATCTATA
•••••••••••••••••••••••••••••••••••••••••••••••••••••••••••••••••• ••••••
AAATATGATGGTAAAGCTACACATGGTCCAAGTGTGAAGAATGCAGTTTACGCCCATCAAATTGAAACAGGTCTATA 310       320       330       340       350       360       370       380
         |         |         |         |         |         |         |         |
TGACGGATGTTATATATCTACGACAACAGACAAGGAAATTGCCAAGAAATTTGCAACAAGCTCCGGCATCGAAAATG
•••••••••••••••••••••••••••••••••••••••••••••••••••••••••••••• ••••••••••••••
TGACGGATGTTATATATCTACGACAACAGACAAGGAAATTGCCAAGAAATTTGCAACAAGTTCCGGCATCGAAAATG 390       400       410       420       430       440       450       460
         |         |         |         |         |         |         |         |
GCTATATATATGTTTTAAATAGAGATTTGTTTGGTCAATATTCTATTTTTGAATATGAGGTTGAACATCCAGAAAAC
•••••••••••••••••••••••• ••••••••••••••••••••••••••••••••••••••••••••••••••
GCTATATATATGTTTTAAATAGGGATTTGTTTGGTCAATATTCTATTTTTGAATATGAGGTTGAACATCCAGAAAAC 470       480       490       500       510       520       530
         |         |         |         |         |         |         |
CCAGATGAGAAGGAAGTAACAATCAGAGCTGAAGATTGTGGCTGTATTCCTGAAGAAGTGATTATTGCTAAAGAGTT
••• •••••••••••••••••••••••••••••••••••••••••••••••••••••••••••••••••••••••
CCAAATGAGAAGGAAGTAACAATCAGAGCTGAAGATTGTGGCTGTATTCCTGAAGAAGTGATTATTGCTAAAGAGTT 540       550       560       570       580       590       600       610
 |         |         |         |         |         |         |         |
GATAGAAATTAACTAAGTTGAAAGGTCAATATAATGGCTTTAGTTGAATTGAAAGTGCCCGACATTGGCGGACACGA
•••••••••••••••••••••••••••••••••••••••••••••••••••••••••••••••••••••••••••
GATAGAAATTAACTAAGTTGAAAGGTCAATATAATGGCTTTAGTTGAATTGAAAGTGCCCGACATTGGCGGACACGA 620       630
    |         |
AAATGTAGATATTATCGC
••••••••••••••••••
AAATGTAGATATTATCGC
```

FIGURE 3

ΔG287-919-His
ΔG287-Orf46.1-His
ΔG287-953-His
ΔG287-961-His
ΔG287-230-His
ΔG287-936-His
ΔG287-287-His
ΔG287$_{nz}$-287$_{nz}$-His
ΔG287$_{nz}$-741$_{MC58}$-His
ΔG287$_{nz}$-741$_{ET37}$-His

ΔG287$_{nz}$-919-His
ΔG287$_{nz}$-953-His
ΔG287$_{nz}$-961-His
ΔG287$_{nz}$-287-His
ΔG287$_{nz}$-287$_{nz}$-His
ΔG287$_{nz}$-741$_{MC58}$-His

ΔG287-919-Orf46.1-His
ΔG287-Orf46.1-919-His
919-287-Orf46-His
Orf46.1-287-919-His 961c-741$_{MC58}$-His
961c-983-His
961c-Orf46.1-His
961cL-741$_{MC58}$
961cL-287
961c-230-His
961c-936-His

ΔG741$_{MC58}$-961c-His
ΔG741$_{MC58}$-961-His
ΔG741$_{MC58}$-983-His
ΔG741$_{MC58}$-Orf46.1-His
ΔG741$_{MC58}$-741$_{MC58}$-His
ΔG741$_{MC58}$-741$_{ET37}$-His 919-287
953-287
919-Orf46.1-His

Orf46.1-287-His
Orf46.1-919-His
Orf46.1-741$_{MC58}$-His
Orf46.1-961-His
Orf46.1-961c-His
Orf46.1-983-His
Orf46.1-936-His
Orf46.1-230-His 230-741$_{MC58}$-His
230-Orf46.1-His
230-961-His
230-961c-His
936-741$_{MC58}$-His
936-Orf46.1-His
936-961-His
936-741$_{ET37}$-His

ΔG983-741$_{MC58}$-His
ΔG983-961c-His
ΔG983-961-His
ΔG983-Orf46.1-His

ISOLATED PROTEIN AND COMPOSITIONS COMPRISING THE PROTEIN

CROSS REFERENCE TO RELATED APPLICATIONS

This application is a Divisional of U.S. patent application Ser. No. 10/488,786, filed Feb. 25, 2005, which is the National Stage of International Patent Application of PCT/IB2002/003904, filed Sep. 6, 2002, which claims the benefit of United Kingdom Patent Application Serial No. 0121591.2, filed Sep. 6, 2001, each of which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002100610SeqList.txt, date recorded: Feb. 3, 2012, size: 5499 KB).

TECHNICAL FIELD

This invention is in the field of protein expression. In particular, it relates to the expression of proteins from *Neisseria* (e.g. *N. gonorrhoeae* or, preferably, *N. meningitidis*).

BACKGROUND ART

References 1 and 2 disclose alternative and improved approaches for the expression of the Neisserial proteins disclosed in references 3 to 6. One such method is to produce 'hybrid' proteins in which two or more Neisserial proteins are expressed as a single polypeptide chain. This approach offers two advantages. First, a protein that may be unstable or poorly expressed on its own can be assisted by adding a suitable hybrid partner that overcomes the problem. Second, commercial manufacture is simplified as only one expression and purification need be employed in order to produce two separately-useful proteins.

It is an object of the present invention to provide further alternative and improved approaches for the expression of Neisserial proteins.

DISCLOSURE OF THE INVENTION

Hybrid Proteins

Thus the invention provides a method for the simultaneous expression of two or more (e.g. 3, 4, 5, 6 or more) Neisserial proteins, in which said two or more proteins are joined such that they are translated as a single polypeptide chain. In general, the hybrid proteins of the invention can be represented by the formula: $NH_2$-A-[-X-L-]$_n$-B—COOH
wherein X is an amino acid sequence, L is an optional linker amino acid sequence, A is an optional N-terminal amino acid sequence, B is an optional C-terminal amino acid sequence, and n is an integer greater than 1.

The value of n is between 2 and x, and the value of x is typically 3, 4, 5, 6, 7, 8, 9 or 10. Preferably n is 2, 3 or 4; it is more preferably 2 or 3; most preferably, n=2.

The -X- Moieties

There are two main groups of hybrid proteins according to the invention. These two groups are not mutually exclusive.

In the first group, each -X- moiety is:
(a) an orf1, orf4, orf25, orf40, orf46.1, orf83, NMB1343, 230, 233, 287, 292, 594, 687, 736, 741, 907, 919, 936, 953, 961 or 983 amino acid sequence;
(b) an amino acid sequence having sequence identity to an amino acid sequence from (a); or
(c) an amino acid sequence comprising a fragment of an amino acid sequence from (a).

A preferred subset of (a) is: orf46.1, 230, 287, 741, 919, 936, 953, 961 and 983. A more preferred subset of (a) is: orf46.1, 287, 741 and 961. FIG. 3 shows preferred hybrid proteins.

In the second group, the hybrid protein comprises a first -X- moiety (-$X_a$-) and a second -X- moiety (-$X_b$-). The -$X_a$- moiety has one of the following amino acid sequences:
(d) the 446 even SEQ IDs (i.e. 2, 4, 6, . . . , 890, 892) disclosed in reference 3.
(e) the 45 even SEQ IDs (i.e. 2, 4, 6, . . . , 88, 90) disclosed in reference 4;
(f) the 1674 even SEQ IDs 2-3020, even SEQ IDs 3040-3114, and all SEQ IDs 3115-3241, disclosed in reference 5;
(g) the 2160 amino acid sequences NMB0001 to NMB2160 from reference 7; or
(h) an amino acid sequence disclosed in reference 1 or reference 2.

The -$X_b$- moiety is related to -$X_a$- such that: (i) -$X_b$- has sequence identity to -$X_a$-, and/or (j) -$X_b$- comprises a fragment of -$X_a$-.

Examples of this second type of hybrid protein include proteins in which two or more -X-moieties are identical, or in which they are variants of the same protein e.g. two polymorphic forms of the same protein may be expressed as -$X_a$-$X_b$-, and three polymorphic forms may be expressed as -$X_a$-$X_b$-$X_c$- etc.

The -$X_a$- and -$X_b$- moieties may be in either order from N-terminus to C-terminus.

The -$X_a$- moiety is preferably an orf1, orf4, orf25, orf40, orf46.1, orf83, NMB1343, 230, 233, 287, 292, 594, 687, 736, 741, 907, 919, 936, 953, 961 or 983 amino acid sequence. The -$X_a$- moiety is more preferably an orf46.1, 230, 287, 741, 919, 936, 953, 961 or 983 amino acid sequence. The -$X_a$- moiety is most preferably an orf46.1, 287, 741 or 961 amino acid sequence.

In proteins where each of the n -X- moieties shares sequence identity to each other -X- moiety, the protein is referred to as a 'tandem protein'. Tandem proteins in which n=2 are preferred.

The degree of 'sequence identity' referred to in (b) and (i) is preferably greater than 50% (eg. 60%, 70%, 80%, 90%, 95%, 99% or more, up to 100%). This includes mutants, homologs, orthologs, allelic variants etc. [e.g. see ref. 8]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered as an indication of functional equivalence.

The 'fragment' referred to in (c) and (j) should consist of least m consecutive amino acids from an amino acid sequence from (a), (d), (e), (f), (g) or (h) and, depending on the particular sequence, m is 7 or more (eg. 8, 10, 12, 14, 16, 18, 20, 25, 30, 35, 40, 50, 60, 70, 80, 90, 100, 150, 200 or more). Preferably the fragment comprises an epitope from an amino acid sequence from (a), (d), (e), (f), (g) or (h). Preferred fragments are those disclosed in references 9 and 10.

Preferred (c) and (j) fragments are C- and/or N-terminal truncations (e.g. Δ1-287, Δ2-287 etc.).

Preferred (b), (c), (i) and (j) sequences omit poly-glycine sequences. This has been found to aid expression [ref. 2]. Poly-glycine sequences can be represented as $(Gly)_g$, where $g \geq 3$ (e.g. 4, 5, 6, 7, 8, 9 or more). If a -X- moiety includes a poly-glycine sequence in its wild-type form, it is preferred to omit this sequence in the hybrid proteins of the invention. This may be by disrupting or removing the $(Gly)_g$—by deletion (e.g. CGGGGS→CGGGS, CGGS, CGS or CS), by substitution (e.g. CGGGGS→CGXGGS, CGXXGS, CGXGXS etc.), and/or by insertion (e.g. CGGGGS→CGGXGGS, CGXGGGS, etc.). Deletion of $(Gly)_g$ is preferred, and deletion of the N-terminus portion of a protein up to and including the poly-glycine sequence (e.g. deletion of residues 1-32 in SEQ ID 1) is referred to herein as 'ΔG'. Poly-glycine omission is particularly useful for proteins 287, 741, 983 and Tbp2 (ΔG287, ΔG741, ΔG983 and ΔGTbp2—references 1 & 2).

Preferred (c) and (j) fragments omit complete protein domains. This is particularly useful for protein 961, 287, and ORF46. Once a protein has been notional divided into domains, (c) and (j) fragments can omit one or more of these domains (e.g. 287B, 287C, 287BC, ORF46$_{1-433}$, ORF46$_{434-608}$, 961c—reference 2; FIGS. 4 and 5 herein).

287 protein has been notionally split into three domains, referred to as A, B & C (see FIG. 5 of reference 2). Domain B aligns with IgA proteases, domain C aligns with transferrin-binding proteins, and domain A shows no strong alignment with database sequences. An alignment of polymorphic forms of 287 is disclosed in reference 8.

ORF46 has been notionally split into two domains—a first domain (amino acids 1-433; ORF46.1) which is well-conserved between species and serogroups, and a second domain (amino acids 434-608) which is not well-conserved. The second domain is preferably deleted, leaving ORF46.1. An alignment of polymorphic forms of ORF46 is disclosed in reference 8.

961 protein has been notionally split into several domains (FIG. 4).

If a -X- moiety has a leader peptide sequence in its wild-type form, this may be included or omitted in the hybrid proteins of the invention. Where the leader peptide is omitted, this is a preferred example of an amino acid sequence within (c) and (j). In one embodiment, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

When n=2, preferred pairs of -X- moieties are: ΔG287 and 230; ΔG287 and 936; ΔG287 and 741; 961c and 287; 961c and 230; 961c and 936; 961cL and 287; 961cL and 230; 961cL and 936; ORF46.1 and 936; ORF46.1 and 230; 230 and 961; 230 and 741; 936 and 961; 936 and 741. When n=2, preferred pairs of -X- moieties for tandem proteins are: ΔG741 and 741; ΔG287 and 287. More specifically, the following combinations of $X_1$ and $X_2$ are preferred when n=2:

| $X_1$ | $X_2$ |
|---|---|
| ΔG287 | 230 |
| ΔG287 | 936 |
| ΔG287 | 741 |
| ΔG287 | 961 |
| ΔG287 | ORF46.1 |
| ΔG287 | 919 |
| ΔG287 | 953 |
| 961c | 287 |
| 961c | 230 |
| 961c | 936 |
| 961c | 741 |
| 961c | 983 |
| 961c | ΔG983 |
| 961c | ORF46.1 |
| 961 | ORF46.1 |
| 961cL | 287 |
| 961cL | 230 |
| 961cL | 936 |
| ORF46.1 | 936 |
| ORF46.1 | 230 |
| ORF46.1 | 741 |
| ORF46.1 | ΔG741 |
| ORF46.1 | 983 |
| ORF46.1 | ΔG983 |
| 230 | 961 |
| 230 | 741 |
| 230 | ΔG741 |
| 936 | 961 |
| 936 | 741 |
| 936 | ΔG741 |
| ΔG741 | 741 |
| ORF46.1 | 983 |
| ΔG741 | ORF46.1 |
| ΔG741 | 983 |
| ΔG741 | 961 |
| ΔG741 | 961c |
| ΔG983 | ORF46.1 |
| ΔG983 | 961 |
| ΔG983 | 961c |
| 230 | ΔG287 |
| 936 | ΔG287 |
| 741 | ΔG287 |
| 961 | ΔG287 |
| ORF46.1 | ΔG287 |
| 919 | ΔG287 |
| 953 | ΔG287 |
| 287 | 961c |
| 230 | 961c |
| 936 | 961c |
| 741 | 961c |
| 983 | 961c |
| ΔG983 | 961c |
| ORF46.1 | 961c |
| ORF46.1 | 961 |
| 287 | 961cL |
| 230 | 961cL |
| 936 | 961cL |
| 936 | ORF46.1 |
| 230 | ORF46.1 |
| 741 | ORF46.1 |
| ΔG741 | ORF46.1 |
| 983 | ORF46.1 |
| ΔG983 | ORF46.1 |
| 961 | 230 |
| 741 | 230 |
| ΔG741 | 230 |
| 961 | 936 |
| 741 | 936 |
| ΔG741 | 936 |
| ΔG287 | 287 |
| 983 | ORF46.1 |
| ORF46.1 | ΔG741 |
| 983 | ΔG741 |
| 961 | ΔG741 |
| 961c | ΔG741 |
| ORF46.1 | ΔG983 |
| 961 | ΔG983 |
| 961c | ΔG983 |

Where 287 is used in full-length form, it is preferably at the C-terminal end of a hybrid protein; if it is to be used at the N-terminus, if is preferred to use a ΔG form of 287. Similarly, Where 741 is used in full-length form, it is preferably at the C-terminal end of a hybrid protein; if it is to be used at the N-terminus, if is preferred to use a ΔG form of 741.

The -L- Moieties

For each n instances of [-X-L-], linker amino acid sequence -L- may be present or absent. For instance, when n=2 the hybrid may be NH$_2$—X$_1$-L$_1$-X$_2$-L$_2$-COOH, NH$_2$—X$_1$—X$_2$—COOH, NH$_2$—X$_1$-L$_1$-X$_2$—COOH, NH$_2$—X$_1$—X$_2$-L$_2$-COOH, etc.

Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID 27), with the Gly-Ser dipeptide being formed from a BamHI restriction site, thus aiding cloning and manipulation, and the Gly$_4$ tetrapeptide being a typical poly-glycine linker.

If X$_{n+1}$ is a ΔG protein and L$_n$ is a glycine linker, this may be equivalent to X$_{n+1}$ not being a ΔG protein and L$_n$ being absent.

The -A- Moiety

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If X$_1$ lacks its own N-terminus methionine, -A- may be a methionine residue.

The -B- Moiety

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance protein stability. Other suitable C-terminal amino acid sequences will be apparent to those skilled in the art.

Polymorphic Forms of Proteins

The invention can use amino acid sequences from any strains of *N. meningitidis*. References to a particular protein (e.g. '287', or 'ORF46.1') therefore include that protein from any strain. Sequence variations between strains are included within (b), (c), (i) and (j).

Reference sequences from *N. meningitidis* serogroup B include:

| Protein | Reference |
| --- | --- |
| orf1 | Ref. 3, SEQ ID 650 |
| orf25 | Ref. 3, SEQ ID 684 |
| orf46 | Ref. 6, SEQ ID 1049 |
| NMB1343 | Ref. 7, NMB1343 |
| 233 | Ref. 5, SEQ ID 860 |
| 292 | Ref. 5, SEQ ID 1220 |
| 687 | Ref. 5, SEQ ID 2282 |
| 741 | Ref. 5, SEQ ID 2536 |
| 919 | Ref. 5, SEQ ID 3070 |
| 953 | Ref. 5, SEQ ID 2918 |
| 983 | Ref. 7, NMB1969 |

-continued

| Protein | Reference |
| --- | --- |
| orf4 | Ref. 3, SEQ ID 218 |
| orf40 | Ref. 4, SEQ ID 4 |
| orf83 | Ref. 3, SEQ ID 314 |
| 230 | Ref. 5, SEQ ID 830 |
| 287 | Ref. 5, SEQ ID 3104 |
| 594 | Ref. 5, SEQ ID 1862 |
| 736 | Ref. 5, SEQ ID 2506 |
| 907 | Ref. 5, SEQ ID 2732 |
| 936 | Ref. 5, SEQ ID 2884 |
| 961 | Ref. 5, SEQ ID 940 |

Reference 8 discloses polymorphic forms of proteins ORF4, ORF40, ORF46, 225, 235, 287, 519, 726, 919 and 953. Polymorphic forms of 961 are disclosed in references 11 & 12. Any of these polymorphic forms may be used in accordance with the present invention.

The sequence listing herein includes polymorphic forms of proteins 741 (SEQ IDs 1-22) and NMB1343 (SEQ IDs 23-24) which have been identified.

Serogroups and Strains

Preferred proteins of the invention comprise -X- moieties having an amino acid sequence found in *N. meningitidis* serogroup B. Within a single protein of the invention, individual -X- moieties may be from one or more strains. Where n=2, for instance, X$_2$ may be from the same strain as X$_1$ or from a different strain. Where n=3, the strains might be (i) X$_1$=X$_2$=X$_3$ (ii) X$_1$=X$_2$≠X$_3$ (iii) X$_1$≠X$_2$=X$_3$ (iv) X$_1$≠X$_2$≠X$_3$ or (v) X$_1$=X$_3$≠X$_2$, etc.

Within serogroup B, preferred -X- moieties are from strains 2996, MC58, 95N477, or 394/98. Strain 95N477 is sometimes referred to herein as 'ET37', this being its electrophoretic type. Strain 394/98 is sometimes referred to herein as 'nz', as it is a New Zealand strain.

Where a form of 287 is used, this is preferably from strain 2996 or from strain 394/98.

Where a form of 741 is used, this is preferably from serogroup B strains MC58, 2996, 394/98, or 95N477, or from serogroup C strain 90/18311.

Where a form of 961 is used, this is preferably from strain 2996.

Strains are indicated as a subscript e.g. 741$_{MC58}$ is protein 741 from strain MC58. Unless otherwise stated, proteins mentioned herein (e.g. with no subscript) are from *N. meningitidis* strain 2996, which can be taken as a 'reference' strain. It will be appreciated, however, that the invention is not in general limited by strain. As mentioned above, general references to a protein (e.g. '287', '919' etc.) may be taken to include that protein from any strain. This will typically have sequence identity to 2996 of 90% or more (eg. 91%, 92%, 93%, 94%, 95%, 96%, 97%, 98%, 99% or more).

Domain-Based Expression of Protein 961

References 1 and 2 disclose how a protein can be notionally divided into domains and how the protein can be manipulated based on these domains. The present invention extends the application of this approach to protein 961 (also known as 'NadA' [11,12]).

In *N. meningitidis* serogroup B strain 2996, NadA has 405 amino acids. This protein has notionally been divided into the following nine domains (FIG. 4):

| Domain name | Amino acids |
| --- | --- |
| 961-1 'L' | 1-23 |
| 961-2 | 24-87 |
| 961-3 | 88-143 |
| 961-4 | 144-180 |

-continued

| Domain name | Amino acids |
|---|---|
| 961-5 | 181-268 |
| 961-6 | 269-286 |
| 961-7 | 287-330 |
| 961-8 | 331-350 |
| 961-9 | 351-405 |

This information can be used to locate the same domains in other forms of 961.

These domains have been deleted from 961 in strain 2996 in various ways (FIG. 5). Preferred fragments of 961 omit one or more of these nine domains e.g. the following:
- 961-2 to 961-5 ('961a')
- 961-6 to 961-9 ('961b')
- 961-1 to 961-8 ('961cL')
- 961-2 to 961-8 ('961c')
- 961-2 to 961-6 and amino acids 287-325 from domain 961-7 ('961d')
- 961-2 to 961-8 and amino acids 351-383 from domain 961-9 ('961Δ1')
- 961-1 to 961-8 and amino acids 351-383 from domain 961-9 ('961Δ1L')
- 961-1 to 961-7 and amino acids 331-343 from domain 961-8 ('961cL-Δaro')
- 961-1 to 961-6 and amino acids 287-315 from domain 961-7 ('961cL-Δcc')
- 961-1 to 961-5 ('961aL')
- 961-1 to 961-4 ('961aL-Δ1')
- 961-1 to 961-3 ('961aL-Δ2')
- 961-1 to 961-2 ('961aL-Δ3')

These thirteen fragments (and sub-fragments thereof missing 1, 2, 3, 4 or 5 amino acids at either or both ends) are preferred (c) and (j) fragments, but they may also be expressed in their own right i.e. not in the form of a hybrid protein of the invention. Thus the invention provides a protein comprising one of these fragments, providing that the protein is not full-length 961 and is not a protein specifically disclosed in reference 1 or 2. This protein may be a fusion protein (e.g. a GST-fusion or a His-tag fusion).

Sequences

The invention also provides a protein having an amino acid sequence from SEQ IDs 1 to 24. It also provides proteins and nucleic acid having sequence identity to these. As described above, the degree of 'sequence identity' is preferably greater than 50% (eg. 60%, 70%, 80%, 90%, 95%, 99% or more).

The invention also provides nucleic acid encoding such proteins.

Furthermore, the invention provides nucleic acid which can hybridise to this nucleic acid, preferably under "high stringency" conditions (eg. 65° C. in a 0.1×SSC, 0.5% SDS solution).

The invention also provides nucleic acid encoding proteins according to the invention.

It should also be appreciated that the invention provides nucleic acid comprising sequences complementary to those described above (eg. for antisense or probing purposes).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

Mixtures

The invention also provides a composition comprising two or more (i.e. 2, 3, 4, 5, 6 or 7) of the following proteins:
(1) 287
(2) 741
(3) ORF46.1
(4) 961
(5) $NH_2$-A-[-X-L-]$_n$-B—COOH, wherein n=2, $X_1$=287, $X_2$=953
(6) $NH_2$-A-[-X-L-]$_n$-B—COOH, wherein n=2, $X_1$=287, $X_2$=919
(7) $NH_2$-A-[-X-L-]$_n$-B—COOH, wherein n=2, $X_1$=287, $X_2$=961

The mixture may include one or both of the following proteins, either in combination with two or more of (1) to (7), or in combination with only one of (1) to (7):
(8) $NH_2$-A-[-X-L-]$_n$-B—COOH, wherein n=2, $X_1$=287, $X_2$=741
(9) $NH_2$-A-[-X-L-]$_n$-B—COOH, wherein n=2, $X_1$=936, $X_2$=741

Where proteins 287 and 741 are included in the mixture (i.e. in protein 1, 2, 5, 6, 7 or 8), they may be in the 'ΔG' form. Where protein 961 is included, it is preferably in the form of '961c' in which the N-terminus leader and C-terminus membrane anchor are absent [e.g. see refs. 1, 2 & 11].

A preferred mixture comprises the following three proteins:
(1) 961c, preferably 961c$_{2996}$ (e.g. SEQ ID 31 herein);
(2) $NH_2$-A-[-X-L-]$_n$-B—COOH, wherein n is 2, -$X_1$- is ΔG287 (preferably ΔG287$_{NZ}$), -$X_2$- is 953 (preferably 953$_{2996}$) lacking its leader peptide, -$L_1$- is GSGGGG, and -A- comprises a N-terminus methionine (e.g. -A- is M or MA) (e.g. SEQ IDs 28 & 29 herein); and
(3) $NH_2$-A-[-X-L-]$_n$-B—COOH, wherein n=2, $X_1$=936 (preferably 936$_{2996}$), $X_2$=ΔG741 (preferably ΔG741$_{MC58}$), $L_1$=GSGGGG (e.g. SEQ ID 30 herein).

The mixtures may also comprise *N. meningitidis* outer membrane vesicles.

Heterologous Host

Whilst expression of the proteins of the invention may take place in *Neisseria*, the present invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeast etc.

Vectors Etc.

The invention provides (a) nucleic acid encoding the proteins described above (b) vectors comprising these nucleic acid sequences (c) host cells containing said vectors (d) compositions comprising the proteins or nucleic acids of the invention, which may be suitable as immunogenic compositions (e.g. vaccines) or as diagnostic reagents (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against *Neisseria* bacteria, and/or (3) a reagent which can raise antibodies against *Neisseria* bacteria and (g) a method of treating a patient, comprising administering to the patient a therapeutically effective amount of these compositions.

Implementing the invention will typically involve the basic steps of: obtaining a first nucleic acid encoding a first protein; obtaining a second nucleic acid encoding a second protein;

and ligating the first and second nucleic acids. The resulting nucleic acid may be inserted into an expression vector, or may already be part of an expression vector.

To improve solubility, purification of hybrid proteins may involve the refolding techniques disclosed herein.

Immunogenic Compositions and Medicaments

The compositions of the invention are preferably immunogenic composition, and are more preferably vaccine compositions. The pH of the composition is preferably between 6 and 7. The pH may be maintained by the use of a buffer. The composition may be sterile.

Vaccines according to the invention may either be prophylactic (i.e. to prevent infection) or therapeutic (i.e. to treat infection), but will typically be prophylactic.

The invention also provides a composition of the invention for use as a medicament. The medicament is preferably able to raise an immune response in a mammal (i.e. it is an immunogenic composition) and is more preferably a vaccine.

The invention also provides the use of a composition of the invention in the manufacture of a medicament for raising an immune response in a mammal. The medicament is preferably a vaccine.

The invention also provides a method for raising an immune response in a mammal comprising the step of administering an effective amount of a composition of the invention. The immune response is preferably protective. The method may raise a booster response.

The mammal is preferably a human Where the vaccine is for prophylactic use, the human is preferably a child (e.g. a toddler or infant); where the vaccine is for prophylactic use, the human is preferably an adult. A vaccine intended for children may also be administered to adults e.g. to assess safety, dosage, immunogenicity, etc.

These uses and methods are preferably for the prevention and/or treatment of a disease caused by a *Neisseria* (e.g. meningitis, septicaemia, gonorrhoea etc.). The prevention and/or treatment of bacterial meningitis is preferred.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose (WO00/56365) and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in *Remington's Pharmaceutical Sciences*.

Immunogenic compositions used as vaccines comprise an immunologically effective amount of antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine may be administered in conjunction with other immunoregulatory agents.

The vaccine may be administered in conjunction with other immunoregulatory agents.

The composition may include other adjuvants in addition to (or in place of) the aluminium salt. Preferred adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in ref. 13), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e g gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg Vaccine 2000, 19, 618-622; Krieg *Curr opin Mol Ther* 2001 3:15-24; Roman et al., *Nat. Med.*, 1997, 3, 849-854; Weiner et al., *PNAS USA*, 1997, 94, 10833-10837; Davis et al., *J. Immunol.*, 1998, 160, 870-876; Chu et al., *J. Exp. Med.*, 1997, 186, 1623-1631; Lipford et al., *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; International patent applications WO96/02555, WO98/16247, WO98/18810, WO98/40100, WO98/55495, WO98/37919 and WO98/52581] i.e. containing at least one CG dinucleotide, with 5-methylcytosine optionally being used in place of cytosine; (8) a polyoxyethylene ether or a polyoxyethylene ester e.g. WO99/52549; (9) a polyoxyethylene sorbitan ester surfactant in combination with an octoxynol (e.g. WO01/21207) or a polyoxyethylene alkyl ether or ester surfactant in combination with at least one additional non-ionic surfactant such as an octoxynol (e.g. WO01/21152); (10) an immunostimulatory oligonucleotide (e.g. a CpG oligonucleotide) and a saponin e.g. WO00/62800; (11) an immunostimulant and a particle of metal salt e.g. WO00/23105; (12) a saponin and an oil-in-water emulsion e.g. WO99/11241; (13) a saponin (e.g. QS21)+3dMPL+IL-12 (optionally +a sterol) e.g. WO98/57659; (14) other substances that act as immunostimulating agents to enhance the efficacy of the composition.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-O-isoglutaminyl-L-alanine-2-(1'-2'-dipalmitoyl-sn-glycero-3-hydroxyphosphoryloxy)-ethylamine MTP-PE), etc.

Further Antigens

Further antigens which can be included in the composition of the invention include:

- an outer-membrane vesicle (OMV) preparation from *N. meningitidis* serogroup B, such as those disclosed in refs. 14, 15, 16, 17 etc.
- a saccharide antigen from *N. meningitidis* serogroup A, C, W135 and/or Y, such as the oligosaccharide disclosed in ref. 18 from serogroup C [see also ref. 19] or the oligosaccharides of ref. 20.
- a saccharide antigen from *Streptococcus pneumoniae* [e.g. refs. 21, 22, 23].
- a protein antigen from *Helicobacter pylori* such as CagA [e.g. 24], VacA [e.g. 24], NAP [e.g. 25], HopX [e.g. 26], HopY [e.g. 26] and/or urease.
- an antigen from hepatitis A virus, such as inactivated virus [e.g. 27, 28].
- an antigen from hepatitis B virus, such as the surface and/or core antigens [e.g. 28, 29].
- an antigen from hepatitis C virus [e.g. 30].
- an antigen from *Bordetella pertussis*, such as pertussis holotoxin (PT) and filamentous haemagglutinin (FHA) from *B. pertussis*, optionally also in combination with pertactin and/or agglutinogens 2 and 3[ e.g. refs. 31 & 32].
- a diphtheria antigen, such as a diphtheria toxoid [e.g. chapter 3 of ref. 33] e.g. the $CRM_{197}$ mutant [e.g. 34].
- a tetanus antigen, such as a tetanus toxoid [e.g. chapter 4 of ref. 33].
- a saccharide antigen from *Haemophilus influenzae* B [e.g. 19].
- an antigen from *N. gonorrhoeae* [e.g. 3, 4, 5].
- an antigen from *Chlamydia pneumoniae* [e.g. 35, 36, 37, 38, 39, 40, 41].
- an antigen from *Chlamydia trachomatis* [e.g. 42].
- an antigen from *Porphyromonas gingivalis* [e.g. 43].
- polio antigen(s) [e.g. 44, 45] such as IPV or OPV.
- rabies antigen(s) [e.g. 46] such as lyophilised inactivated virus [e.g. 47, RabAvert™]
- measles, mumps and/or rubella antigens [e.g. chapters 9, 10 & 11 of ref. 33].
- influenza antigen(s) [e.g. chapter 19 of ref. 33], such as the haemagglutinin and/or neuraminidase surface proteins.
- an antigen from *Moraxella catarrhalis* [e.g. 48].
- a protein antigen from *Streptococcus agalactiae* (group B streptococcus) [e.g. 49, 50].
- a saccharide antigen from *Streptococcus agalactiae*
- an antigen from *Streptococcus pyogenes* (group A streptococcus) [e.g. 50, 51, 52].
- an antigen from *Staphylococcus aureus* [e.g. 53].

The composition may comprise one or more of these further antigens.

Where a saccharide or carbohydrate antigen is used, it is preferably conjugated to a carrier protein in order to enhance immunogenicity [e.g. refs. 54 to 63]. Preferred carrier proteins are bacterial toxins or toxoids, such as diphtheria or tetanus toxoids. The $CRM_{197}$ diphtheria toxoid is particularly preferred. Other suitable carrier proteins include the *N. meningitidis* outer membrane protein [e.g. ref. 64], synthetic peptides [e.g. 65, 66], heat shock proteins [e.g. 67], pertussis proteins [e.g. 68, 69], protein D from *H. influenzae* [e.g. 70], toxin A or B from *C. difficile* [e.g. 71], etc. Where a mixture comprises capsular saccharides from both serogroups A and C, it is preferred that the ratio (w/w) of MenA saccharide: MenC saccharide is greater than 1 (e.g. 2:1, 3:1, 4:1, 5:1, 10:1 or higher). Saccharides from different serogroups of *N. meningitidis* may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or genetic means [32]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens are preferably mixed with (and more preferably adsorbed to) an aluminium salt (e.g. phosphate, hydroxide, hydroxyphosphate, oxyhydroxide, orthophosphate, sulphate). The salt may take any suitable form (e.g. gel, crystalline, amorphous etc.).

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 72 to 80]. Protein components of the compositions of the invention may thus be replaced by nucleic acid (preferably DNA e.g. in the form of a plasmid) that encodes the protein.

Definitions

The term "comprising" means "including" as well as "consisting" e.g. a composition "comprising" X may consist exclusively of X or may include something additional e.g. X+Y.

The term "about" in relation to a numerical value x means, for example, x±10%.

BRIEF DESCRIPTION OF DRAWINGS

FIG. 1 shows an alignment of twenty-three sequences for protein 741. These are SEQ IDs 1 to 22 plus the sequence from MC58.

FIG. 2 shows an alignment of the NMB1343 sequence from gonococcus (top; SEQ ID 25) and meningococcus (bottom; SEQ ID 26).

FIG. 3 shows hybrid and tandem proteins of the invention.

MODES FOR CARRYING OUT THE INVENTION

Hybrid Proteins—$X_1=\Delta G287$

Figure 4:
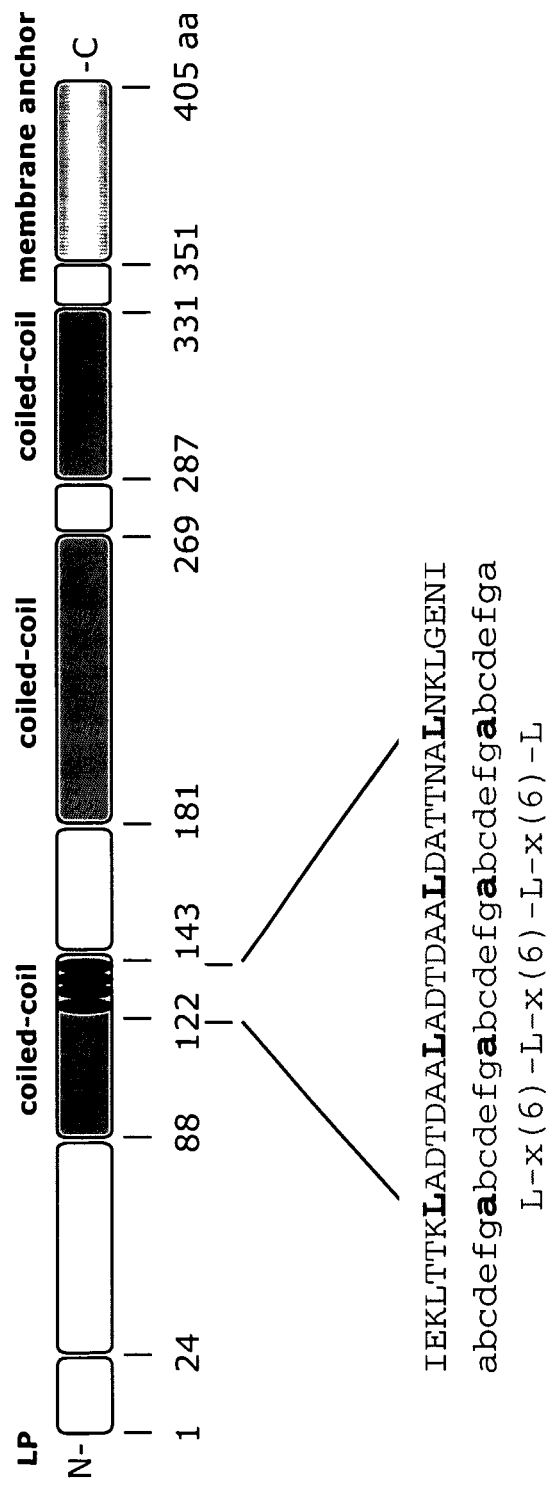
FIG. 4 shows 9 domains within $961_{2996}$.

In addition to those disclosed in references 1 & 2, seven hybrid proteins with ΔG287 from strain 2996 at the N-terminus were constructed. Eight 287 tandem proteins were also made (see below).

| # | n | $X_1$ | $L_1$ | $X_2$ | $L_2$ |
|---|---|---|---|---|---|
| 1 | 2 | ΔG287 | — | 230 | $(His)_6$ |
| 2 | 2 | | — | 936 | $(His)_6$ |
| 3 | 2 | | — | $741_{MC58}$ | $(His)_6$ |
| 4 | 2 | | — | $741_{ET37}$ | $(His)_6$ |
| 5 | 2 | | — | $741_{90/18311}$ | $(His)_6$ |
| 6 | 2 | | — | $741_{95N477}$ | $(His)_6$ |
| 7 | 2 | $\Delta G287_{nz}$ | — | $741_{MC58}$ | $(His)_6$ |

These proteins were adjuvanted with either Freund's complete adjuvant (FCA) or 3 mg/ml alum and used to immunise mice. The resulting sera were tested against various Neisserial strains using the bactericidal assay. Titres using protein #3 were as follows:

| Strain (serogroup) | 2996 (B) | MC58 (B) | NGH38 (B) | 394/98 (B) | 44/76 (B) | F6124 (A) |
|---|---|---|---|---|---|---|
| Al hydroxide | 8192 | 32768 | 8192 | >2048 | 16384 | 8192 |
| FCA | 16384 | 262144 | 8192 | >2048 | >32768 | 8192 |

In further experiments using protein #3 adjuvanted with aluminium hydroxide, anti-287 and anti-741 ELISA titres each exceeded 984150 and BCA titres were as follows:

| 2996 (B) | MC58 (B) | NGH38 (B) | 394/98 (B) | 44/76 (B) | F6124 (A) | BZ133 (C) |
|---|---|---|---|---|---|---|
| 8000 | 65000 | 4000 | 4000 | 32000 | 8000 | 16000 |

Results obtained after immunisation with proteins disclosed in refs. 1 & 2, tested against the homologous strain, were as follows:

| n | $X_1$ | $L_1$ | $X_2$ | $L_2$ | Bactericidal titre FCA | Bactericidal titre Alum | ELISA FCA | ELISA Alum |
|---|---|---|---|---|---|---|---|---|
| 2 | $\Delta G287_{394/98}$ | — | 961 | $(His)_6$ | — | 32768 | — | >109350 |
| | | | 919 | | 32768 | 4096 | 4718 | 3678 |
| | | | 953 | | >32768 | >16384 | 1900 | 6936 |
| | | | 741 | | 16384 | 2048 | 232 | 862 |
| 2 | $\Delta G287_{2996}$ | — | 961 | $(His)_6$ | 65536 | 32768 | 108627 | >109350 |
| | | | 919 | | 128000 | 32000 | 11851 | 2581 |
| | | | 953 | | 65536 | — | 3834 | — |
| | | | 741 | | 16384 | 8192 | 315 | 4645 |

Hybrid Proteins—$X_1$=961c or 961cL

In addition to those disclosed in references 1 & 2, eight hybrid proteins with either 961c or 961cL (i.e. 961c+leader peptide) at the N-terminus were constructed:

| # | n | $X_1$ | $L_1$ | $X_2$ | $L_2$ |
|---|---|---|---|---|---|
| 1 | 2 | 961c | — | 287 | — |
| 2 | 2 | | — | 287 | $(His)_6$ |
| 3 | 2 | | — | 230 | $(His)_6$ |
| 4 | 2 | | — | 936 | $(His)_6$ |
| 5 | 2 | 961cL | — | 287 | — |
| 6 | 2 | | — | 287 | $(His)_6$ |
| 7 | 2 | | — | 230 | $(His)_6$ |
| 8 | 2 | | — | 936 | $(His)_6$ |

These proteins were adjuvanted with either Freund's complete adjuvant (FCA) or 3.3 mg/ml alum and used to immunise mice. The resulting sera were tested against various Neisserial strains using the bactericidal assay. Titres using protein #8 were as follows:

| Strain (serogroup) | 2996 (B) | MC58 (B) | 394/98 (B) | 44/76 (B) | F6124 (A) |
|---|---|---|---|---|---|
| Al hydroxide | 8192 | 8192 | 512 | 1024 | <16 |
| FCA | 65536 | 16384 | >2048 | >2048 | 8192 |

Titres obtained after immunisation with 961c-741[ refs. 1 & 2] were as follows:

| Strain (serogroup) | 2996 (B) | MC58 (B) | 394/98 (B) | 44/76 (B) | F6124 (A) | BZ133 (C) |
|---|---|---|---|---|---|---|
| Al hydroxide | 65536 | 32768 | 4096 | >32768 | 16384 | >2048 |
| FCA | >16384 | 262144 | 4096 | >16384 | — | >2048 |

These results could be improved by mixing 961c-741 with ORF46.1 or with ΔG287-919.

Results obtained after immunisation with proteins disclosed in refs. 1 & 2, tested against the homologous strain, were as follows:

| n | $X_1$ | $L_1$ | $X_2$ | $L_2$ | Bactericidal titre FCA | Bactericidal titre Alum | ELISA FCA | ELISA Alum |
|---|---|---|---|---|---|---|---|---|
| 2 | 961c | — | ORF46.1 | $(His)_6$ | 32768 | 1024 | >109350 | >109350 |
| | | | 741 | | >16384 | 8192 | >109350 | >109350 |
| | | | 936 | | >32768 | 8192 | >109350 | >109350 |

Hybrid Proteins—$X_1$=ORF46.1

In addition to those disclosed in references 1 & 2, two hybrid proteins with ORF46.1 at the N-terminus were constructed:

| # | n | $X_1$ | $L_1$ | $X_2$ | $L_2$ |
|---|---|-------|-------|-------|-------|
| 1 | 2 | ORF46.1 | — | 936 | $(His)_6$ |
| 2 | 2 | ORF46.1 | — | 230 | $(His)_6$ |

These proteins were adjuvanted with either Freund's complete adjuvant (FCA) or 3 mg/ml alum and used to immunise mice. The resulting sera were tested against the homologous strain using the bactericidal assay and by ELISA.

Results obtained after immunisation with proteins disclosed in refs. 1 & 2 were as follows:

| | | | | | Bactericidal titre | | ELISA | |
|---|---|---|---|---|---|---|---|---|
| n | $X_1$ | $L_1$ | $X_2$ | $L_2$ | FCA | Alum | FCA | Alum |
| 2 | ORF46.1 | — | 961 | $(His)_6$ | 8192 | 8192 | 21558 | >109350 |
|   |         | — | 961c | $(His)_6$ | 8192 | 128 | 9020 | 76545 |

Hybrid Proteins—$X_1$=230

In addition to those disclosed in references 1 & 2, four hybrid proteins with 230 at the N-terminus were constructed:

| # | n | $X_1$ | $L_1$ | $X_2$ | $L_2$ |
|---|---|-------|-------|-------|-------|
| 1 | 2 | 230 | — | ORF46.1 | $(His)_6$ |
| 2 | 2 |     | — | 961 | $(His)_6$ |
| 3 | 2 |     | — | 961c | $(His)_6$ |
| 4 | 2 |     | — | $741_{MC58}$ | $(His)_6$ |

Hybrid Proteins—$X_1$=936

In addition to those disclosed in references 1 & 2, seven hybrid proteins with 936 at the N-terminus were constructed:

| # | n | $X_1$ | $L_1$ | $X_2$ | $L_2$ |
|---|---|-------|-------|-------|-------|
| 1 | 2 | 936 | — | ORF46.1 | $(His)_6$ |
| 2 | 2 |     | — | 961 | $(His)_6$ |
| 3 | 2 |     | — | $741_{ET37}$ | $(His)_6$ |
| 4 | 2 |     | — | $741_{MC58}$ | $(His)_6$ |
| 5 | 2 |     | — | $741_{90/18311}$ | $(His)_6$ |
| 6 | 2 |     | — | $741_{95N477}$ | $(His)_6$ |
| 7 | 2 |     | — | 741 | $(His)_6$ |

These proteins were adjuvanted with either Freund's complete adjuvant (FCA) or 3 mg/ml alum and used to immunise mice. The resulting sera were tested against various Neisserial strains using the bactericidal assay. Titres using protein #2 were as follows:

| Strain(serogroup) | $2996^{(B)}$ | $MC58^{(B)}$ | $394/98^{(B)}$ | $44/76^{(B)}$ | $F6124^{(A)}$ |
|---|---|---|---|---|---|
| Al hydroxide | 16384 | 32768 | 1024 | 2048 | <16 |
| FCA | 65536 | 65536 | >2048 | 8192 | 2048 (36%) |

Titres using protein #4 were as follows:

| Strain(serogroup) | $2996^{(B)}$ | $MC58^{(B)}$ | $394/98^{(B)}$ | $44/76^{(B)}$ | $F6124^{(A)}$ |
|---|---|---|---|---|---|
| Al hydroxide | 256 | >262144 | >2048 | 32768 | 8192 |
| FCA | 1024 | >262144 | >2048 | >32768 | >32768 |

Titres using protein #7 were as follows:

| Strain (serogroup) | $2996^{(B)}$ | $MC58^{(B)}$ | $394/98^{(B)}$ | $44/76^{(B)}$ | $F6124^{(A)}$ | $BZ133^{(C)}$ |
|---|---|---|---|---|---|---|
| Al hydroxide | 256 | 130000 | 16000 | 32000 | 8000 | 16000 |

Results obtained after immunisation with proteins disclosed in refs. 1 & 2, tested against the homologous strain, were as follows:

| | | | | | Bactericidal titre | | ELISA | |
|---|---|---|---|---|---|---|---|---|
| n | $X_1$ | $L_1$ | $X_2$ | $L_2$ | FCA | Alum | FCA | Alum |
| 2 | 936 | — | 741 | $(His)_6$ | 1024 | 256 | 1466 | 5715 |
|   |     |   | 936 |           | >32768 | >32768 | >109350 | >109350 |

Mixtures of Hybrid Proteins

Mice were immunised with of three proteins adjuvanted with aluminium hydroxide, either single or in a triple combination: (1) $287_{NZ}$-953; (2) 936-741; and (3) 961c. The mixture was able to induce high bactericidal titres against various strains:

|     | $2996^{(B)}$ | $MC58^{(B)}$ | NGH38 | $394/98^{(B)}$ | $1144/76^{(B)}$ | $F6124^{(A)}$ | $BZ133^{(C)}$ | $C11^{(C)}$ |
|---|---|---|---|---|---|---|---|---|
| (1) | 32000 | 16000 | 130000 | 16000 | 32000 | 8000 | 16000 | 8000 |
| (2) | 256 | 131000 | 128 | 16000 | 32000 | 8000 | 16000 | <4 |
| (3) | 32000 | 8000 | — | — | — | 8000 | — | 32000 |
| mix | 32000 | 32000 | 65000 | 16000 | 260000 | 65000 | >65000 | 8000 |
| (X) | 4000 | 4000 | 1000 | 1000 | >4000 | 1000 | 4000 | n.d. |

'—' indicates that this strain contains no NadA gene
(X) was a combination of protein 287 with outer membrane vesicles, for comparison Looking at individual mice, the mixture induced high and consistent bactericidal titres:

| #      | 1     | 2     | 3     | 4     | 5     | 6     | 7     | 8     | 9     | 10    |
|--------|-------|-------|-------|-------|-------|-------|-------|-------|-------|-------|
| 2996   | 32768 | 16384 | 65536 | 32768 | 32768 | 65536 | 65536 | 32768 | 65536 | 8192  |
| MC58   | 65536 | 32768 | 65536 | 65536 | 65536 | 8192  | 65536 | 32768 | 32768 | 65536 |
| 394/98 | 65536 | 4096  | 16384 | 4096  | 8192  | 4096  | 32768 | 16384 | 8192  | 16384 |

Tandem Proteins

Hybrid proteins of the invention can be represented by formula NH$_2$-[- X-L-]-COOH. Where all n instances of -X- are the same basic protein (either identical, or the same protein from different strains or species), the protein is referred to as a 'tandem' protein.

thus amino acid sequence SEQ ID 23; GenBank AAF41718) was identical in all 10 strains.

NMB1343 was also detected in two strains of *N. gonorrhoeae* (F62 and SN4). The amino acid sequence from gonococcus is SEQ ID 24. An alignment with the meningococcal sequence is:

```
            . . . .10 . . . .20 . . . .30 . . . .40 . . . .50
Ng   1:INNLWEIS LYRGISCQQDEQNNGQLKPKGNKAEVAIRYDGKFKYDGKAT : 50
Nm   1:~~~~~MGNFLYRGISCQQDEQNNGQLKPKGNKAEVAIRYDGKFKYDGKAT : 45

. . . .60 . . . .70 . . . .80 . . . .90 . . . 100
Ng  51:HGPSVKNAVYAHQIETDLYDGCYISTTTDKEIAKKFATSSGIENGYIYVL :100
Nm  46:HGPSVKNAVYAHQIETGLYDGCYISTTTDKEIAKKFATSSGIENGYIYVL : 95

. . . 110 . . . 120 . . . 130 . . . 140 . . . 150
Ng 101:NRDLFGQYSIFEYEVEHPENP EKEVTIRAEDCGCIPEEVIIAKELIEIN :150
Nm  96:NRDLFGQYSIFEYEVEHPENPNEKEVTIRAEDCGCIPEEVIIAKELIEIN :145
```

Twelve specific tandem proteins are:

| #  | n | X$_1$ | L$_1$ | X$_2$ | L$_2$ |
|----|---|-------|-------|-------|-------|
| 1  | 2 | ΔG741$_{MC58}$ | — | 741$_{MC58}$ | (His)$_6$ |
| 2  | 2 | ΔG287$_{2996}$ | (Gly)$_6$ | ΔG287$_{394/98}$ | (His)$_6$ |
| 3  | 2 | ΔG287$_{2996}$ | (Gly)$_6$ | ΔG287$_{2996}$ | (His)$_6$ |
| 4  | 2 | ΔG287$_{394/98}$ | (Gly)$_6$ | ΔG287$_{394/98}$ | (His)$_6$ |
| 5  | 2 | ΔG287$_{394/98}$ | (Gly)$_6$ | ΔG287$_{2996}$ | (His)$_6$ |
| 6  | 2 | ΔG287$_{2996}$ | (Gly)$_6$ | ΔG287$_{394/98}$ | — |
| 7  | 2 | ΔG287$_{2996}$ | (Gly)$_6$ | ΔG287$_{2996}$ | — |
| 8  | 2 | ΔG287$_{394/98}$ | (Gly)$_6$ | ΔG287$_{394/98}$ | — |
| 9  | 2 | ΔG287$_{394/98}$ | (Gly)$_6$ | ΔG287$_{2996}$ | — |
| 10 | 2 | ΔG741$_{MC58}$ | — | 741$_{394/98}$ | (His)$_6$ |
| 11 | 2 | ΔG741$_{MC58}$ | — | 741$_{90/18311}$ | (His)$_6$ |
| 12 | 2 | ΔG741$_{MC58}$ | — | 741$_{95N477}$ | (His)$_6$ |

Proteins #1 to #5 have all been expressed in soluble form in *E. coli*. Expression levels were between 0.24 and 0.50 mg protein per litre of culture. The tandem proteins were purified and mixed with aluminium phosphate as an adjuvant. Tandem proteins #2, #4 and #5 adsorbed readily to aluminium phosphate; adsorption was less complete for tandem proteins #1 and #3.

Allelic Variants—741

Twenty-two polymorphic sequences of 741 were found (SEQ IDs 1 to 22). These and the MC58 sequence are aligned in FIG. 1.

Allelic Variants—NMB1343

Using PCR on 42 strains of meningococcus of various serogroups, the gene encoding NMB1343 protein was found in 24/42 and was absent in 18/42 strains (Table 1). The NMB1343 gene was sequenced for 10 of the NMB1343$^+$ strains (Table 1, column 3). The nucleic acid sequence (and An alignment of the corresponding nucleotide sequences is shown in FIG. 2. This shows that the gonococcal sequence has a 4mer insertion in the 5' region of the NMB1343 gene which causes a frameshift and consequent loss of the 5' methionine residue.

Domain Deletion—961

961 is not present in the *N. meningitidis* serogroup A genome sequence [81], even though the surrounding regions are conserved (>90%) between serogroups A and B. References 11 and 12 disclose polymorphic forms of 961. The gene was found to be present in 91% of serogroup B strains belonging to hypervirulent lineages ET-5, ET-37 and cluster A4, but was absent in all strains of lineage 3 tested. Most of the serogroup C strains tested were positive even if not belonging to hypervirulent lineages. The same was true for the serogroup B strains with serotype 2a and 2b. For serogroup A, one strain belonging to subgroup III was positive whereas the other two strains belonging to subgroup IV-1 were negative. 961 was absent in *N. gonorrhoeae* and in commensal species *N. lactamica* and *N. cinerea*.

Figure 5:
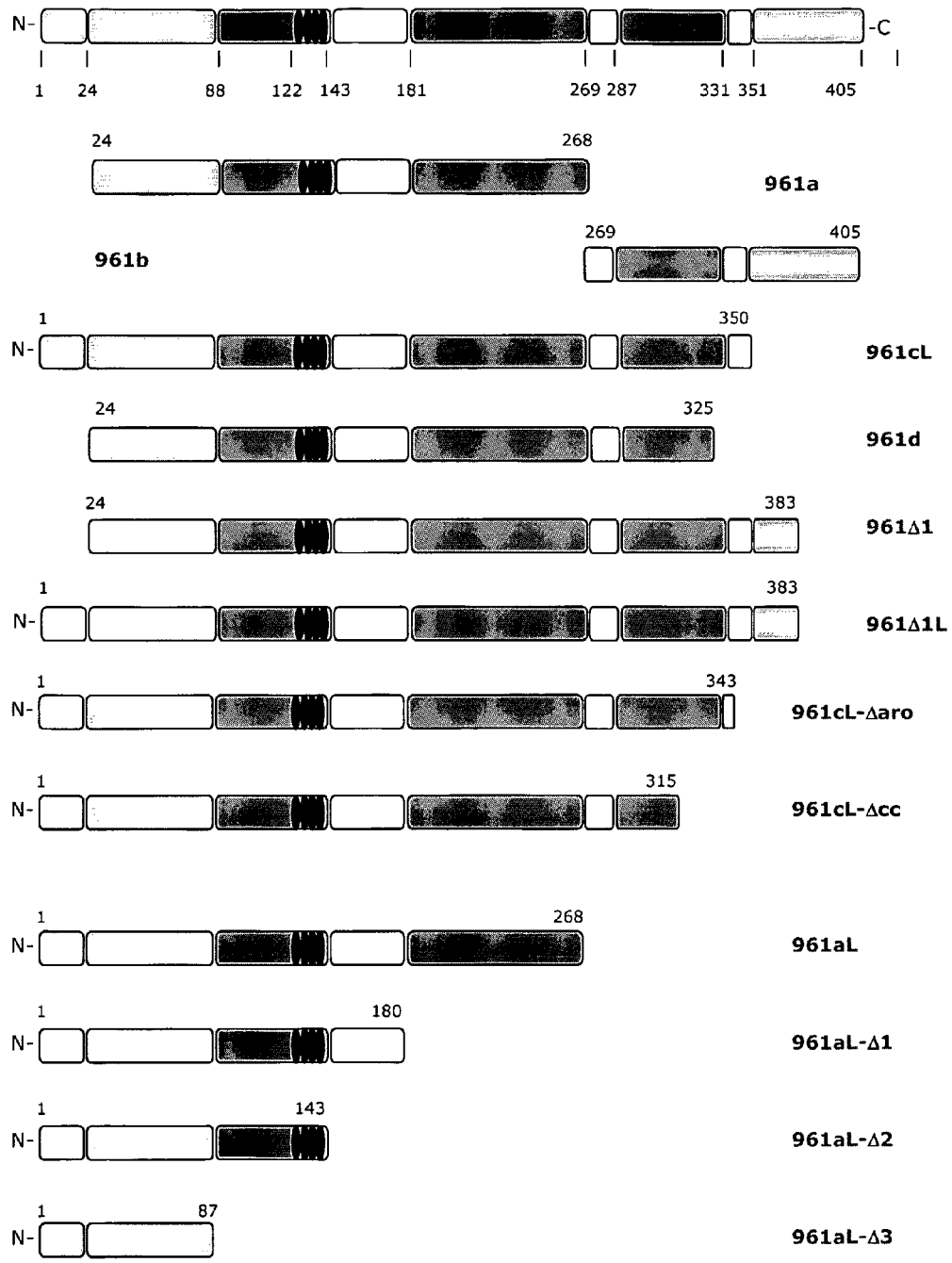
FIG. 5 shows how these have been manipulated.

FIGS. 4 and 5 show domains in protein 961.

When the anchor region (domain 9) of protein 961 is deleted ('961cL') and expressed in *E. coli*, the protein is exported in the periplasm and secreted in the supernatant of the culture.

To investigate this further, deletion mutants in the C-terminal region of 961 were constructed (961cL-Δaro, 961cLΔcc, 961aL, 961aL-Δ1, 961aL-Δ2, 961aL-Δ3) on the basis of structural features (deletions of aromatic residues in the cases of 961cΔaro mutant, and of coiled-coil regions for the others). These were analysed for expression and secretion into the periplasm and the supernatant of the culture. In all of these deletion mutants, the protein is produced in large amount, is present in periplasmic fraction, and is released in the supernatant of the culture.

ΔG287—Cross-Strain Bactericidal Activity 287 was cloned for five different *N. meningitidis* serogroup B strains and was manipulated to delete the N-terminus up to the end of the poly-glycine region and to introduce a C-terminal his-tag. This gave five ΔG287 proteins. These were adjuvanted with FCA and used to raise immune sera in mice, which were then tested for bactericidal activity against all five serogroup B strains and also against serogroup A and C strains. Bactericidal titres were as follows:

| Protein strain | Sera tested for bactericidal activity against strain * | | | | | | |
|---|---|---|---|---|---|---|---|
| | 2996 | BZ232 | MC58 | 1000 | 394/98 | F6124 | BZ133 |
| 2996 | 16000 | 128 | 4096 | 4096 | 1024 | 8000 | 16000 |
| BZ232 | >8000 | 256 | 2048 | 8000 | 2048 | 16000 | 8000 |
| MC58 | >8000 | 64 | >8000 | 8000 | 2048 | 8000 | 8000 |
| 1000 | >8000 | 64 | 4096 | 8000 | 1024 | 16000 | 16000 |
| 394/98 | >16000 | 128 | 16000 | >2048 | >16000 | — | — |

* titres against homologous strain shown in bold

Refolding

To improve the levels of soluble protein for some hybrid proteins, alternative refolding protocols to those disclosed in reference 2 were adopted.

Inclusion bodies (IBs) were isolated as follows:
1. Homogenize cells (5 g wet weight) in 25 ml 0.1 M Tris-HCl pH 7, 1 mM EDTA, at 4° C. using an ultraturrax (10 000 rpm)
2. Add 1.5 mg lysozyme per gram cells, mix shortly with an ultraturrax, and incubate at 4° C. for 30 min.
3. Use sonication or high-pressure homogenization (French press) to disrupt the cells.
4. To digest DNA, add $MgCl_2$ to a final concentration of 3 mM and DNase to a final concentration of 10 µg/ml, and incubate for 30 min at 25° C.
5. Add 0.5 vol. 60 mM EDTA, 6% Triton X-100, 1.5M NaCl pH7, to the solution, and incubate for 30 min at 4° C.
6. Spin down inclusion bodies by centrifugation at 31000 g (20 000 rpm) for 10 min, 4° C.
7. Resuspend pellet in 40 ml 0.1 M tris-HCl pH 7, 20 mM EDTA, using an ultraturrax
8. Repeat centrifugation step 6.
9. The inclusion body pellet may be used, or stored frozen at −20° C.

Hybrid proteins were expressed in *E. coli* as follows:

| Protein | Culture volume (litres) | Flask volume (litres) | Temp (° C.) | Final $OD_{600}$ | Inclusion body yield (w/w) |
|---|---|---|---|---|---|
| ORF46.1-961-His | 1 | 2 | 37 | 1.51 | 33.2% |
| ORF46.1-961c-His | 1 | 2 | 37 | 1.6 | 28.3% |
| 961c-ORF46.1His | 1 | 2 | 37 | 1.18 | 23.5% |
| orf46.1-741 His | 5 | 5 | 37 | 12.42 | 35.2 |

The pellets were solubilised, refolded, ultrafiltered, dialysed, and protein was then purified:

ORF46.1-961-His IBs were solubilised as follows: IB proteins were resuspended in 4 ml of 6M guanidine HCl, 1 mM EDTA pH 8.5 buffer, to a final protein concentration of 1 mg/ml. To refold the protein, 2 ml of solubilised protein was diluted in 400 ml of refolding buffer (0.1M Tris HCl, 1M L-arginine, 2 mM EDTA pH 8.2) and incubated for 1 hour at 15° C., resulting in a protein concentration of 5 µg/ml. Subsequently, another 2 ml of the solubilised protein was added and incubated for an additional hour at the same temperature resulting in a final protein concentration of 10 µg/ml. The material was ultrafiltered using a 300 ml Amicon ultrafiltration cell (8400), applying a 3 bar pressure on an Amicon membrane with a 30 kDa cut-off (YM30) resulting in 130 ml final volume. The ultrafiltered material was dialysed using a regenerated cellulose tubular membrane with a 12-14 kDa cutoff (Cellusep—Step bio) for 24 hours against 10 L of 0.1M Tris HCl pH 8.2 buffer. A second dialysis of 24 h against 10 L of 300 mM NaCl, 50 mM sodium phosphate pH 8.0 buffer was performed. The dialysed material was centrifuged at 22000 rpm for 45 minutes at 4° C. in a Beckman centrifuge rotor JA25.5 The supernatant isolated after centrifugation was used for His-tag purification.

orf 46.1-961c-His IBs were solubilised as follows: IB proteins were resuspended in 4 ml of 6M guanidine HCl, 1 mM EDTA pH 8.5 buffer, to a final protein concentration of 1 mg/ml. To refold the protein, 2 ml of the solubilised protein was diluted in 400 ml refolding buffer (0.5M Tris HCl, 1M L-arginine, 2 mM EDTA pH 8.2) and incubated for 1 h at 15° C., resulting in a protein concentration of 5 µg/ml. Subsequently another 2 ml of the solubilised protein was added and incubated for an additional hour at the same temperature resulting in a final protein concentration of 10 µg/ml. The material was ultrafiltered using a 300 ml Amicon ultrafiltration cell (8400), applying a 3 bar pressure on an Amicon membrane with a 30 kDa cut-off (YM30) resulting in 150 ml final volume. The ultrafiltered material was dialysed using a regenerated cellulose tubular membrane with a 12-14 kDa cutoff (Cellusep—Step bio) for 24 h against 10 L of 0.1M Tris HCl pH 8.2 buffer. A second dialysis of 24 h against 10 L of 300 mM NaCl, 50 mM sodium phosphate pH 8.0 buffer was performed. The dialysed material was centrifuged at 22000 rpm for 45 minutes at 4° C. in a Beckman centrifuge rotor JA25.5. The supernatant isolated after centrifugation was used for His-tag purification.

961c-orf46.1-His IBs were solubilised as follows: IB proteins were resuspended in 4 ml of 6M guanidine HCl, 1 mM EDTA pH 8.5 buffer, to a final protein concentration of 1 mg/ml. To refold the protein, 2 ml of the solubilised protein was diluted in 400 ml refolding buffer (0.1M Tris HCl, 0.5 M L-arginine, 2 mM EDTA pH 8.2) and incubated for 1 h at 15° C., resulting in a protein concentration of 5 µg/ml. Subsequently another 2 ml of the solubilized protein was added and incubated for an additional hour at the same temperature resulting in a final protein concentration of 10 µg/ml. The material was ultrafiltered using a 300 ml Amicon ultrafiltration cell (8400), applying a 3 bar pressure on an Amicon membrane with a 30 kDa cut-off (YM30) resulting in 150 ml final volume. The ultrafiltered material was dialysed using a regenerated cellulose tubular membrane with a 12-14 kDa cutoff (Cellusep—Step bio) for 24 h against 10 L of 0.1M Tris HCl pH 8.2 buffer. A second dialysis of 24 h against 10 L of 300 mM NaCl, 50 mM sodium phosphate pH 8.0 buffer was performed. The dialysed material was centrifuged at 22000 rpm for 45 minutes at 4° C. in a Beckman centrifuge rotor JA25.5. The supernatant isolated after centrifugation was used for His-tag purification.

orf46.1-741-His IBs were solubilised as follows: IB proteins were resuspended in 4 ml of 6M guanidine HCl, 1 mM EDTA pH 8.5 buffer, to a final protein concentration of 10 mg/ml. To refold, 2 ml of the solubilised protein was diluted in 400 ml of the refolding buffer (0.5M Tris HCl, 0.7 M L-arginine, 2 mM EDTA pH 7.2) and incubated for 1 h at 15° C., resulting in a protein concentration of 50 µg/ml. Subsequently another 2 ml of the solubilised protein was added and incubated for an additional hour at the same temperature resulting in a final protein concentration of 100 µg/ml. The material was ultrafiltered using a 300 ml Amicon ultrafiltration cell (8400), applying a 3 bar pressure on an Amicon membrane with a 30 kDa cut-off (YM30) resulting in 120 ml final volume. The ultrafiltered material was dialysed using a regenerated cellulose tubular membrane with a 12-14 kDa cutoff (Cellusep—Step bio) for 24 h against 10 L of 0.1M Tris HCl pH 8.2 buffer. A second dialysis of 24 h against 10 L of 300 mM NaCl, 50 mM sodium phosphate pH 8.0 buffer was performed. The dialysed material was centrifuged at 22000 rpm for 45 minutes at 4° C. in a Beckman centrifuge rotor JA25.5 The supernatant isolated after centrifugation was used for His-tag purification.

Compared with proteins purified as described in ref. 2, bactericidal assay titres were as follows:

| Protein | Reference 2 CFA | Reference 2 Aluminium hydroxide | Refolded Aluminium hydroxide | Refolded MF59 | Refolded Aluminium phosphate |
|---|---|---|---|---|---|
| ORF46.1-961-His | 8192 | 8192 | 32768 | — | — |
| ORF46.1-961c-His | 8192 | 128 | <64 | 8192 | — |
| 961c-ORF46.1His | 32768 | 1024 | 16384 | — | — |
| orf46.1-741 His | <4 | 16 | <4 | 256 | — |

Similar procedures were used for ORF46.1 to purify the protein from IBs when expressed with no His-tag ('ORF46.1K'):

| Protein | Culture volume (litres) | Flask volume (litres) | Temp (° C.) | Final $OD_{600}$ | Inclusion body yield (w/w) |
|---|---|---|---|---|---|
| orf46.1K | 5 | 5 | 37 | 13.7 | 29.4 |

IB proteins were resuspended in 4 ml of 6M guanidine HCl, 1 mM EDTA pH 8.5 buffer, to a final protein concentration of 10 mg/ml. To refold, 2 ml of the solubilised protein was diluted in 400 ml of the refolding buffer (0.5M Tris HCl, 0.7 M L-arginine, 2 mM EDTA pH 7.2) and incubated for 1 hours at 15° C., resulting in a protein concentration of 50 µg/ml. Subsequently another 2 ml of the solubilised protein was added and incubated for an additional hour at the same temperature resulting in a final protein concentration of 100 µg/ml. The material was ultrafiltered using a 300 ml Amicon ultrafiltration cell (8400), applying a 3 bar pressure on an Amicon membrane with a 30 kDa cut-off (YM30) resulting in 120 ml final volume. The ultrafiltered material was dialysed using a regenerated cellulose tubular membrane with a 12-14 kDa cutoff (Cellusep—Step bio) for 12 h against 10 L of 50 mM sodium phosphate, 2 mM EDTA, pH 7.2 buffer. A second dialysis of 24 h against 10 L of the same buffer was performed. The dialysed material was centrifuged at 22000 rpm for 45 minutes at 4° C. in a Beckman centrifuge rotor JA25.5. The supernatant isolated after centrifugation was used for cationic exchange chromatography. The purification was done on a AKTA explorer chromatography system (Amersham-Pharmacia Biotech) using a 5 ml HiTrap SP sepharose HP column (Amersham-Pharmacia Biotech). The flow rate applied was of 1.5 ml per minute. The column was washed with 35 ml of 50 mM sodium phosphate buffer pH 7.2. A linear gradient (0-1 M NaCl) was performed using a 50 mM sodium phosphate buffer pH 7.2. The protein eluted in two peaks at 92 mM and 380 mM NaCl. The fractions constituting each peak were pooled and respectively named pool 1 and pool 2.

Compared with proteins purified as described in ref. 2, bactericidal assay titres when adjuvanted with aluminium hydroxide were improved from <4 to 1024. The titre using aluminium phosphate adjuvant with the refolded protein was 2048. ELISA titres were as follows:

| Protein | Aluminium adjuvant | Elisa (M7) | SBA (2996) |
|---|---|---|---|
| Orf46.1k (pool 1) | Hydroxide 3.3 mg/ml | 1212 | 512 |
|  | Phosphate 0.6 mg/ml | 154 | 1024 |
| Orf46.1k (pool 2) | Hydroxide 3.3 mg/ml | 1085 | 1024 |
|  | Phosphate 0.6 mg/ml | 250 | 1024 |

It will be understood that the invention has been described by way of example only and modifications may be made whilst remaining within the scope and spirit of the invention.

TABLE 1

| Strain | 1343 | Sequence | Strain classification |
|---|---|---|---|
| 72/00 | + |  | ET5 B:15:P1.7,13,13a |
| 30/00 | + |  | ET5 B:15:P1.7,16 |
| 39/99 | + |  | ET5 C:15:P1.7,16 |
| 95330 | + |  | ET5 B:4:P1.15 |
| M4102 | + |  | ET5 nd |
| MC58(21) | + | + | ET5 B:15:P1.7,16b |
| BZ169(7) | + | + | ET5 B:NT:P1.16 |
| BZ83(19) | + |  | ET5 B:15:—.— |
| CU385 | + | + | ET5 B:4:P1.15 |
| 220173I | + |  | ET5 NG:4:P1.15 |
| 64/96 | + | + | ET5 NG:15:P1.7,16 (carrier) |
| 220173I | + |  | ET5 B:4:P1.15 (carrier) |
| ISS1071 | + |  | nd B:15:P1.7,16 (ET5?) |
| BZ198(2) | + | + | lin.3 B:8:P1.1 |
| 980-2543 | + | + | lin.3 B:NT:P1.4 |
| 16060 | + | + | other B:4:P1.14 (carrier) |
| 394-98 | + |  | nd B:4:P1.4 (lin 3?) |
| ISS1106 | + |  | nd B:4:P1.4 (lin.3?) |
| BZ133(10) | + | + | sub I B:NT:—.— |
| S3446 | + | + | nd B:14:P1.23,14 |
| ISS1001 | + | + | nd B:14:P1.13 |
| 241175I | + |  | other NG:21:P1.16 (carrier) |
| 171274I | + |  | other NG:15:— (carrier) |
| 66/96 | + |  | other B:17:P1.15 (carrier) |
| 961-5945 | − |  | A4 |
| 96217 | − |  | A4 |
| 312294 | − |  | A4 |
| 90/18311(24) | − |  | ET37 |
| 93/4286(25) | − |  | ET37 |
| M986 | − |  | ET37 |
| 1000(5) | − |  | other |
| NGE28(13) | − |  | other carrier |
| NGH38(14) | − |  | other carrier |
| BZ232(18) | − |  | other |
| F6124(23) | − |  | sub III A:—.— |
| C11 | − |  | C:— |
| NMB | − |  | nd |
| 8047 | − |  | nd |
| ISS759 | − |  | nd C:2b:P1.2 |
| ISS1113 | − |  | nd C:2:P1.5 |
| 65/96 | − |  | nd 4:P1.14 |
| 2996(96) | − |  | nd B:2b:P1.5,2 |

REFERENCES (The Contents of which are Hereby Incorporated by Reference)

1—International patent application WO01/64920.
2—International patent application WO01/64922.

3—International patent application WO99/24578.
4—International patent application WO99/36544.
5—International patent application WO99/57280.
6—International patent application WO00/22430.
7—Tettelin et al. (2000) *Science* 287:1809-1815.
8—International patent application WO00/66741.
9—International patent application WO00/71574.
10—International patent application WO01/04316
11—International patent application PCT/IB02/03396.
12—Comanducci et al. (2002) *J Exp Med* 195:1445-1454.
13—*Vaccine Design: subunit & adjuvant approach* (1995) Powell & Newman (ISBN: 030644867X).
14—International patent application WO01/52885.
15—Bjune et al. (1991) *Lancet* 338(8775): 1093-1096.
16—Fukasawa et al. (1999) *Vaccine* 17:2951-2958.
17—Rosenqvist et al. (1998) *Dev. Biol. Stand.* 92:323-333.
18—Costantino et al. (1992) *Vaccine* 10:691-698.
19—Costantino et al. (1999) *Vaccine* 17:1251-1263.
20—International patent application PCT/IB02/03191.
21—Watson (2000) *Pediatr Infect Dis J* 19:331-332.
22—Rubin (2000) *Pediatr Clin North Am* 47:269-285, v.
23—Jedrzejas (2001) *Microbiol Mol Biol Rev* 65:187-207.
24—International patent application WO93/18150.
25—International patent application WO99/53310.
26—International patent application WO98/04702.
27—Bell (2000) *Pediatr Infect Dis J* 19:1187-1188.
28—Iwarson (1995) *APMIS* 103:321-326.
29—Gerlich et al. (1990) *Vaccine* 8 Suppl:S63-68 & 79-80.
30—Hsu et al. (1999) *Clin Liver Dis* 3:901-915.
31—Gustafsson et al. (1996) *N. Engl. J. Med.* 334:349-355.
32—Rappuoli et al. (1991) *TIBTECH* 9:232-238.
33—*Vaccines* (1988) eds. Plotkin & Mortimer. ISBN 0-7216-1946-0.
34—Del Guidice et al. (1998) *Molecular Aspects of Medicine* 19:1-70.
35—International patent application WO02/02606.
36—Kalman et al. (1999) *Nature Genetics* 21:385-389.
37—Read et al. (2000) *Nucleic Acids Res* 28:1397-406.
38—Shirai et al. (2000) *J. Infect. Dis.* 181 (Suppl 3):S524-S527.
39—International patent application WO99/27105.
40—International patent application WO00/27994.
41—International patent application WO00/37494.
42—International patent application WO99/28475.
43—Ross et al. (2001) *Vaccine* 19:4135-4142.
44—Sutter et al. (2000) *Pediatr Clin North Am* 47:287-308.
45—Zimmerman & Spann (1999) *Am Fam Physician* 59:113-118, 125-126.
46—Dreesen (1997) *Vaccine* 15 Suppl:S2-6.
47—*MMWR Morb Mortal Wkly Rep* 1998 Jan. 16; 47(1):12, 19.
48—McMichael (2000) *Vaccine* 19 Suppl 1:S101-107.
49—Schuchat (1999) *Lancet* 353(9146):51-6.
50—WO02/34771.
51—Dale (1999) *Infect Dis Clin North Am* 13:227-43, viii.
52—Ferretti et al. (2001) *PNAS USA* 98: 4658-4663.
53—Kuroda et al. (2001) *Lancet* 357(9264):1225-1240; see also pages 1218-1219.
54—Ramsay et al. (2001) *Lancet* 357(9251):195-196.
55—Lindberg (1999) *Vaccine* 17 Suppl 2:S28-36.
56—Buttery & Moxon (2000) *J R Coll Physicians Lond* 34:163-168.
57—Ahmad & Chapnick (1999) *Infect Dis Clin North Am* 13:113-133, vii.
58—Goldblatt (1998) *J. Med. Microbiol.* 47:563-567.
59—European patent 0 477 508.
60—U.S. Pat. No. 5,306,492.
61—International patent application WO98/42721.
62—*Conjugate Vaccines* (eds. Cruse et al.) ISBN 3805549326, particularly vol. 10:48-114.
63—Hermanson (1996) *Bioconjugate Techniques* ISBN: 0123423368 or 012342335X.
64—European patent application 0372501.
65—European patent application 0378881.
66—European patent application 0427347.
67—International patent application WO93/17712.
68—International patent application WO98/58668.
69—European patent application 0471177.
70—International patent application WO00/56360.
71—International patent application WO00/61761.
72—Robinson & Tones (1997) *Seminars in Immunology* 9:271-283.
73—Donnelly et al. (1997) *Annu Rev Immunol* 15:617-648.
74—Scott-Taylor & Dalgleish (2000) *Expert Opin Investig Drugs* 9:471-480.
75—Apostolopoulos & Plebanski (2000) *Curr Opin Mol Ther* 2:441-447.
76—Ilan (1999) *Curr Opin Mol Ther* 1:116-120.
77—Dubensky et al. (2000) *Mol Med* 6:723-732.
78—Robinson & Pertmer (2000) *Adv Virus Res* 55:1-74.
79—Donnelly et al. (2000) *Am J Respir Crit Care Med* 162 (4 Pt 2):5190-193.
80—Davis (1999) *Mt. Sinai J. Med.* 66:84-90.
81—Parkhill et al. (2000) *Nature* 404:502-506.

```
                          SEQUENCE LISTING

SEQ ID 1 - 741 from strain 1000
MIRSKPVNRTAFCCLSLTAALILTACSSGGGGVAADIGAGLADALTTPLDHKDKSLQSLILDQSVRKNEK
LKLAAQGAEKTYGNGDSLNIGKLKNDKVSRFDFIRQIEVDGQIITLASGEFQIYKQNHSAVVALQIEKIN
NPDKIDSLINQRSFLVSGLGGEHTAFNQLPDGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 2 - 741 from strain 2201731
(premature stop codon, though reliable sequence)
MIRSKPVNRTAFCCLSLITALILTACSSGGGGVAADIGAGLADALTAPLDHKDKGLQSLTLDQSVRKNEK
LKLAAQGAEKTYGNGDSLNTGKLKNDKVSRFDFIRQIEVDGQLITLESGEFQVYKQSHSALTAFQTEQIQ
DSEHSGKMVAKRQFRIGDIAGEHTSFDKLPEGGRATYRGTAFGSDDAGGKLTYTIDFAAKQGNGKIEHLK
SPELNVDLAAADIKPDGKRHAVISGSVLYNQAEKGSYSLGIFGGKA SEQ ID 3 - 741 from strain 90/18311 (incomplete)
GLADALTAPLDHKDKSLQSLILDQSVRKNEKLKLAAQGAEKTYGNGDSLNIGKLKNDKVSRFDFIRQIEV
DGQLITLESGEFQIYKQDHSAVVALQIEKINNPDKIDSLINQRSFLVSGLGGEHTAFNQLPSGKAEYHGK
AFSSDDPNGRLHYSIDFIKKQGYGRIEHLKTPEQNVELASAELKADEKSHAVILGDTRYGGEEKGTYHLA
LFGDRAQEIAGSATVKIREKVHET
```

SEQUENCE LISTING

```
SEQ ID 4 - 741 from strain L93/4286 (incomplete)
VAADIGAGLADALTAPLDHKDKGLQSLMLDQSVRKNEKLKLAAQGAEKTYGNGDSLNIGKLKNDKVSRFD
FIRQIEVDGQIITLASGEFQIYKQNHSAVVALQIEKINNPDKIDSLINQRSFLVSGLGGEHTAFNQLPDG
KAEYHGKAFSSDDPNGRLHYSIDFIKKQGYGRIEHLKTPEQNVELASAELKADEKSHAVILGDTRYGGEE
KGTYHLALFGDRAQEIAGSATVKIREKVHEIGIAGKQ SEQ ID 5 - 741 from strain 2996
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLESGEFQIYKQDHSAVVALQIEKIN
NPDKIDSLINQRSFLVSGLGGEHTAFNQLPDGKAEYHGKAFSSDDAGGKLTYTIDFAAKQGHGKIEHLKT
PEQNVELAAAELKADEKSHAVILGDTRYGSEEKGTYHLALFGDRAQEIAGSATVKIGEKVHEIGIAGKQ SEQ ID 6 - 741 from strain 30/00
KDKGLQSLILDQSVRKNEKLKLAAQGAEKTYGNGDSLNIGKLKNDKVSRFDFIRQIEVDGQLITLESGEF
QVYKQSHSALTAFQTEQIQDSEHSGKMVAKRQFRIGDIAGEHTSFDKLPEGGRATYRGTAFGSDDAGGKL
TYTIDFAAKQGNGKIEHLKSPELNVDLAAADIKPDGKRHAVISGSVLYNQAEKGSYSLGIFGGKAQEVAG
SAEVKTVNGIRHIGLAAKQ SEQ ID 7 - 741 from strain 312294
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLESGEFQIYKQDHSAVVALQIEKIN
NPDKIDSLINQRSFLVSGLGGEHTAFNQLPDGKAEYHGKAFSSDDAGGKLTYTIDFAAKQGHGKIEHLKT
PEQNVELAAAELKADEKSHAVILGDTRYGSEEKGTYHLALFGDRAQEIAGSATVKIGEKVHEIGIAGKQ SEQ ID 8 - 741 from strain 39/99 (incomplete)
DKGLQSLTLDQSVRKNEKLKLAAQGAEKTYGNGDSLNTGKLKNDKVSRFDFIRQIEVDGQLITLESGEFQ
VYKQSHSALTAFQTEQIQDSEHSGKMVAKRQFRIGDIAGEHTSFDKLPEGGRATYRGTAFGSDDAGGKLT
YTIDFAAKQGNGKIEHLKSPELNVDLAAADIKPDGKRHAVISGSVLYNQAEKGSYSLGIFGGKAQEVAGS
AEVKTVNGIRHIGLAAKQ SEQ ID 9 - 741 from strain 5/99
MTRSKPVNRTAFCCLSLTAALILTACSSGGGGVAADIGAGLADALTAPLDHKDKGLQSLTLDQSVRKNEK
LKLAAQGAEKTYGNGDSLNTGKLKNDKVSRFDFIRQIEVDGQLITLESGEFQIYKQDHSAVVALQIEKIN
NPDKIDSLINQRSFLVSGLGGEHTAFNQLPSGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 10 - 741 from strain 67/00
MTRSKPVNRTAFCCFSLTAALILTACSSGGGGVAADIGAGLADALTAPLDHKDKSLQSLTLDQSVRKNEK
LKLAAQGAEKTYGNGDSLNTGKLKNDKVSRFDFIRQIEVDGQLITLESGEFQVYKQSHSALTALQTEQEQ
DPEHSGKMVAKRRFKIGDIAGEHTSFDKLPKDVMATYRGTAFGSDDAGGKLTYTIDFAAKQGHGKIEHLK
SPELNVELATAYIKPDEKHHAVISGSVLYNQDEKGSYSLGIFGGQAQEVAGSAEVETANGIHHIGLAAKQ SEQ ID 11 - 741 from strain BZ169
LQSLTLDQSVRKNEKLKLAAQGAEKTYGNGDSLNTGKLKNDKVSRFDFIRQIEVDGQLITLESGEFQVYK
QSHSALTAFQTEQIQDSEHSGKMVAKRQFRIGDIAGEHTSFDKLPEGGRATYRGTAFGSDDAGGKLTYTI
DFAAKQGNGKIEHLKSPELNVDLAAADIKPDGKRHAVISGSVLYNQAEKGSYSLGIFGGKAQEVAGSAEV
KTVNGIRHIGLAAKQ SEQ ID 12 - 741 from strain 72/00
LQSLTLDQSVRKNEKLKLAAQGAEKTYGNGDSLNTGKLKNDKVSRFDFIRQIEVDGQLITLESGEFQVYK
QSHSALTAFQTEQIQDSEHSGKMVAKRQFRIGDIAGEHTSFDKLPEGGRATYRGTAFGSDDAGGKLTYTI
DFAAKQGNGKIEHLKSPELNVDLAAADIKPDGKRHAVISGSVLYNQAEKGSYSLGIFGGKAQEVAGSAEV
KTVNGIRHIGLAAKQ SEQ ID 13 - 741 from strain 93/114
MTRSKPVNRTAFCCFSLTAALILTACSSGGGGVAADIGAGLADALTAPLDHKDKSLQSLTLDQSVRKNEK
LKLAAQGAEKTYGNGDSLNTGKLKNDKVSRFDFIRQIEVDGQLITLESGEFQVYKQSHSALTALQTEQEQ
DPEHSGKMVAKRRFKIGDIAGEHTSFDKLPKDVMATYRGTAFGSDDAGGKLTYTIDFAAKQGHGKIEHLK
SPELNVELATAYIKPDEKHHAVISGSVLYNQDEKGSYSLGIFGGQAQEVAGSAEVETANGIHHIGLAAKQ SEQ ID 14 - 741 from strain 95N477
MTRSKPVNRTAFCCLSLTAALILTACSSGGGGVAADIGAGLADALTAPLDHKDKSLQSLTLDQSVRKNEK
LKLAAQGAEKTYGNGDSLNTGKLKNDKVSRFDFIRQIEVDGQLITLESGEFQIYKQDHSAVVALQIEKIN
NPDKIDSLINQRSFLVSGLGGEHTAFNQLPSGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 15 - 741 from strain 96217
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLESGEFQIYKQDHSAVVALQIEKIN
NPDKIDSLINQRSFLVSGLGGEHTAFNQLPDGKAEYHGKAFSSDDAGGKLTYTIDFAAKQGHGKIEHLKT
PEQNVELAAAELKADEKSHAVILGDTRYGSEEKGTYHLALFGDRAQEIAGSATVKIGEKVHEIGIAGKQ SEQ ID 16 - 741 from strain BZ133
MIRSKPVNRTAFCCLSLTAALILTACSSGGGGVAADIGAGLADALTAPLDHKDKSLQSLILDQSVRKNEK
LKLAAQGAEKTYGNGDSLNTGKLKNDKVSRFDFIRQIEVDGQLITLESGEFQVYKQSHSALTALQTEQVQ
DSEHSGKMVAKRQFRIGDIAGEHTSFDKLPEGGRATYRGTAFGSDDASGKLTYTIDFAAKQGHGKIEHLK
SPELNVDLAASDIKPDKKRHAVISGSVLYNQAEKGSYSLGIFGGQAQEVAGSAEVETANGIRHIGLAAKQ
```

SEQUENCE LISTING

SEQ ID 17 - 741 from strain BZ232
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLASGEFQIYKQNHSAVVALQIEKIN
NPDKIDSLINQRSFLVSGLGGEHTAFNQLPDGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 18 - 741 from strain Cl 1
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLESGEFQIYKQDHSAVVALQIEKIN
NPDKIDSLINQRSFLVSGLGGEHTAFNQLPSGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 19 - 741 from strain M1090
MIRSKPVNRTAFCCLSLTAALILTACSSGGGGVAADIGAGLADALTAPLDHKDKSLQSLILDQSVRKNEK
LKLAAQGAEKTYGNGDSLNIGKLKNDKVSRFDFIRQIEVDGQLITLESGEFQIYKQDHSAVVALQIEKIN
NPDKIDDSLINQRSFLVSGLGGEHTAFNQLPSGKAEYHGKAFSSDDAGGKLTYTIDFAAKQGHGKIEHLKT
PEQNVELASAELKADEKSHAVILGDTRYGGEEKGTYHLALFGDRAQEIAGSATVKIREKVHEIGIAGKQ SEQ ID 20 - 741 from strain M1096
MIRSKPVNRTAFCCLSLTAALILTACSSGGGGVAADIGAGLADALTTPLDHKDKSLQSLILDQSVRKNEK
LKLAAQGAEKTYGNGDSLNIGKLKNDKVSRFDFIRQIEVDGQIITLASGEFQIYKQNHSAVVALQIEKIN
NPDKIDSLINQRSFLVSGLGGEHTAFNQLPDGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 21 - 741 from strain M198/172
MIRSKPVNRTAFCCLSLTAALILTACSSGGGGVAADIGAGLADALTAPLDHKDKSLQSLILDQSVRKNEK
LKLAAQGAEKTYGNGDSLNTGKLKNDKVSRFDFIRQIEVDGQLITLESGEFQVYKQSHSALTALQTEQVQ
DSEHSGKMVAKRQFRIGDIAGEHTSFDKLPEGGRATYRGTAPGSDDASGKLTYTIDFAAKQGHGKIEHLK
SPELNVDLAASDIKPDKKRHAVISGSVLYNQAEKGSYSLGIFGGQAQEVAGSAEVETANGIRHIGLAAKQ SEQ ID 22 - 741 from strain NGH38
MTRSKPVNRTAFCCLSLTAALILTACSSGGGGVAADIGAGLADALTAPLDHKDKSLQSLTLDQSVRKNEK
LKLAAQGAEKTYGNGDSLNTGKLKNDKVSRFDFIRQIEVDGQTITLASGEFQIYKQNHSAVVALQIEKIN
NPDKIDSLINQRSFLVSGLGGEHTAFNQLPDGKAEYHGKAFSSDDPNGRLHYSIDFTKKQGYGRIEHLKT
PEQNVELASAELKADEKSHAVILGDTRYGGEEKGTYHLALFGDRAQEIAGSATVKIREKVHEIGIAGKQ SEQ ID 23 - NMB1343 from ten meningococcal strains
MGNFLYRGISCQQDEQNNGQLKPKGNKAEVAIRYDGKFKYDGKATHGPSVKNAVYAHQIETGLYDGCYIS
TTTDKEIAKKFATSSGIENGYIYVLNRDLFGQYSIFEYEVEHPENPNEKEVTIRAEDCGCIPEEVITAKE
LIEIN SEQ ID 24 - NMB1343 from gonococcus
INNLWEISYLYRGISCQQDEQNNGQLKPKGNKAEVAIRYDGKFKYDGKATHGPSVKNAVYAHQIETDLYD
GCYISTTTDKEIAKKFATSSGIENGYIYVLNRDLFGQYSIFEYEVEHPENPDEKEVTIRAEDCGCIPEEV
IIAKELTEIN SEQ ID 25 - NMB1343 nucleic acid sequence (gonococcus)
TCCGCCGCATTACCTTATAAAATAAAACATCCCTCTCAAGCAGTCTGATAATGTTTGGATTGCTTGAGAT
TGATGATGATGGTGTTAAATTCAACCTTTAAATTAATAACTTATGGGAAATTTCTTATTTATATAGAGG
CATTAGTTGCCAACAAGATGAGCAAAATAATGGACAGTTAAAACCTAAAGGTAATAAAGCTGAAGTTGCA
ATTCGTTATGATGGTAAGTTTAAATATGATGGTAAAGCTACACATGGTCCAAGTGTGAAGAATGCAGTTT
ACGCCCATCAAATTGAAACAGATCTATATGACGGATGTTATATATCTACGACAACAGACAAGGAAATTGC
CAAGAAATTTGCAACAAGCTCCGGCATCGAAAATGGCTATATATATGTTTTAAATAGAGATTTGTTTGGT
CAATATTCTATTTTTGAATATGAGGTTGAACATCCAGAAAACCCAGATGAGAAGGAAGTAACAATCAGAG
CTGAAGATTGTGGCTGTATTCCTGAAGAAGTGATTATTGCTAAAGAGTTGATAGAAATTAACTAAGTTGA
AAGGTCAATATAATGGCTTTAGTTGAATTGAAAGTGCCCGACATTGGCGGACACGAAAATGTAGATATTA
TCGC SEQ ID 26 - NMB1343 nucleic acid sequence (meningococcus)
TCCGCCGCATTACCTTATAAAATAAAACATCCCTCTCAAGCAGTCTGATAATGTTTGGATTGCTTGAGAT
TGATGATGATGGTGTTAAATTCAACCTTTAAATTAATAACTTATGGGAAATTTCTTTATATAGAGGCATT
AGTTGCCAACAAGATGAGCAAAATAATGGACAGTTAAAACCTAAAGGTAATAAAGCTGAAGTTGCAATTC
GTTATGATGGTAAGTTTAAATATGATGGTAAAGCTACACATGGTCCAAGTGTGAAGAATGCAGTTTACGC
CCATCAAATTGAAACAGGTCTATATGACGGATGTTATATATCTACGACAACAGACAAGGAAATTGCCAAG
AAATTTGCAACAAGTTCCGGCATCGAAAATGGCTATATATATGTTTAAATAGGGATTTGTTTGGTCAAT
ATTCTATTTTTGAATATGAGGTTGAACATCCAGAAAACCCAAATGAGAAGGAAGTAACAATCAGAGCTGA
AGATTGTGGCTGTATTCCTGAAGAAGTGATTATTGCTAAAGAGTTGATAGAAATTAACTAAGTTGAAAGG
TCAATATAATGGCTTTAGTTGAATTGAAAGTGCCCGACATTGGCGGACACGAAAATGTAGATATTATCGC SEQ ID 27 - linker
GSGGGG SEQ ID 28 - preferred ΔG287-953 hybrid
MASPDVKSADTLSKPAAPVVAEKETEVKEDAPQAGSQGQGAPSTQGSQDMAAVSAENTGNGGAATTDKPK
NEDEGPQNDMPQNSAESANQTGNNQPADSSDSAPASNPAPANGGSNFGRVDLANGVLIDGPSQNITLTHC
KGDSCNGDNLLDEEAPSKSEFENLNESERIEKYKKDGKSDKFTNLVATAVQANGTNKYVIIYKDKSASSS
SARFRRSARSRRSLPAEMPLIPVNQADTLIVDGEAVSLTGHSGNIFAPEGNYRYLTYGAEKLPGGSYALR

```
SEQUENCE LISTING

VQGEPAKGEMLAGTAVYNGEVLHFHTENGRPYPTRGRFAAKVDFGSKSVDGIIDSGDDLHMGTQKFKAAI
DGNGFKGTWTENGGGDVSGRFYGPAGEEVAGKYSYRPTDAEKGGFGVFAGKKEQDGSGGGGATYKVDEYH
ANARFAIDHFNTSTNVGGFYGLTGSVEFDQAKRDGKIDITIPVANLQSGSQHFTDHLKSADIFDAAQYPD
IRFVSTKFNFNGKKLVSVDGNLTMHGKTAPVKLKAEKFNCYQSPMAKTEVCGGDFSTTIDRTKWGVDYLV
NVGMTKSVRIDIQIEAAKQ

SEQ ID 29 - ΔG287NZ-953 hybrid
MASPDVKSADTLSKPAAPVVSEKETEAKEDAPQAGSQGQGAPSAQGGQDMAAVSEENTGNGGAAATDKPK
NEDEGAQNDMPQNAADTDSLTPNHTPASNMPAGNMENQAPDAGESEQPANQPDMANTADGMQGDDPSAGG
ENAGNTAAQGTNQAENNQTAGSQNPASSTNPSATNSGGDFGRTNVGNSVVIDGPSQNITLTHCKGDSCSG
NNFLDEEVQLKSEFEKLSDADKISNYKKDGKNDGKNDKFVGLVADSVQMKGINQYIIFYKPKPTSFARFR
RSARSRRSLPAEMPLIPVNQADTLIVDGEAVSLTGHSGNIFAPEGNYRYLTYGAEKLPGGSYALRVQGEP
SKGEMLAGTAVYNGEVLHFHTENGRPSPSRGRFAAKVDFGSKSVDGIIDSGDGLHMGTQKFKAAIDGNGF
KGTWTENGGGDVSGKFYGPAGEEVAGKYSYRPTDAEKGGFGVFAGKKEQDGSGGGGATYKVDEYHANARF
AIDHFNTSTNVGGFYGLTGSVEFDQAKRDGKIDITIPVANLQSGSQHFTDHLKSADIFDAAQYPDIRFVS
TKFNFNGKKLVSVDGNLTMHGKTAPVKLKAEKFNCYQSPMAKTEVCGGDFSTTIDRTKWGVDYLVNVGMT
KSVRIDIQIEAAKQ SEQ ID 30 - 936 - ΔG741 hybrid
MKPKPHTVRTLIAAIFSLALSGCVSAVIGSAAVGAKSAVDRRTTGAQTDDNVMALRIETTARSYLRQNNQ
TKGYTPQISVVGYNRHLLLLGQVATEGEKQFVGQIARSEQAAEGVYNYITVASLPRTAGDIAGDTWNTSK
VRATLLGISPATQARVKIVTYGNVTYVMGILTPEEQAQITQKVSTTVGVQKVITLYQNYVQRGSGGGVA
ADIGAGLADALTAPLDHKDKGLQSLTLDQSVRKNEKLKLAAQGAEKTYGNGDSLNTGKLKNDKVSRFDFI
RQIEVDGQLITLESGEFQVYKQSHSALTAFQTEQIQDSEHSGKMVAKRQFRIGDIAGEHTSFDKLPEGGR
ATYRGTAFGSDDAGGKLTYTIDFAAKQGNGKIEHLKSPELNVDLAAADIKPDGKRHAVISGSVLYNQAEK
GSYSLGIFGGKAQEVAGSAEVKTVNGIRHIGLAAKQ SEQ ID 31 - 961c
MATNDDDVKKAATVAIAAAYNNGQEINGFKAGETIYDIDEDGTITKKDATAADVEADDFKGLGLKKVVTN
LTKTVNENKQNVDAKVKAAESEIEKLTTKLADTDAALADTDAALDATTNALNKLGENITTFAEETKTNIV
KIDEKLEAVADTVDKHAEAFNDIADSLDETNTKADEAVKTANEAKQTAEETKQNVDAKVKAAETAAGKAE
AAAGTANTAADKAEAVAAKVTDIKADIATNKDNIAKKANSADVYTREESDSKFVRIDGLNATTEKLDTRL
ASAEKSIADHDTRLNGLDKTVSDLRKETRQGLAEQAALSGLFQPYNVG
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08840907B2). An electronic copy of the "Sequence Listing" will also be available from the USPTO upon request and payment of the fee set forth in 37 CFR 1.19(b)(3).

What is claimed:

1. A composition comprising an isolated *Neisseria meningitidis* protein having 80% or greater sequence identity to the amino acid sequence of SEQ ID NO: 19 adsorbed to an aluminum salt adjuvant.

2. A composition comprising an isolated *Neisseria meningitidis* protein having 80% or greater sequence identity to the amino acid sequence of SEQ ID NO: 19, and an aluminum hydroxyphosphate adjuvant.

* * * * *